(12) United States Patent
Yilmaz

(10) Patent No.: US 11,622,679 B2
(45) Date of Patent: Apr. 11, 2023

(54) MOUTHPIECE

(71) Applicant: MedikEquip LLC, Seattle, WA (US)

(72) Inventor: Hakan Yilmaz, Seattle, WA (US)

(73) Assignee: Hakan Yilmaz, Tacoma, WA (US)

( * ) Notice: Subject to any disclaimer, the term of this patent is extended or adjusted under 35 U.S.C. 154(b) by 0 days.

(21) Appl. No.: 17/385,170

(22) Filed: Jul. 26, 2021

(65) Prior Publication Data
US 2023/0022562 A1 Jan. 26, 2023

(51) Int. Cl.
*A61B 1/32* (2006.01)
*A61B 1/267* (2006.01)

(52) U.S. Cl.
CPC .............. *A61B 1/32* (2013.01); *A61B 1/267* (2013.01)

(58) Field of Classification Search
CPC ...... A61B 1/32; A61B 1/267; A61M 16/0493; A61M 16/0497
USPC ................................. 600/184–249
See application file for complete search history.

(56) References Cited

U.S. PATENT DOCUMENTS

| 1,798,194 | A |   | 3/1931 | Dodge |  |
|---|---|---|---|---|---|
| 2,969,059 | A | * | 1/1961 | Meek | A61B 1/24 |
|  |  |  |  |  | 600/242 |
| 3,813,096 | A | * | 5/1974 | Welch | A63B 23/032 |
|  |  |  |  |  | 482/11 |
| 4,151,837 | A | * | 5/1979 | Millard, Jr. | A61B 1/24 |
|  |  |  |  |  | 600/226 |
| 5,527,261 | A | * | 6/1996 | Monroe | A61B 1/05 |
|  |  |  |  |  | 600/172 |
| 5,570,704 | A | * | 11/1996 | Buzzard | A61F 5/566 |
|  |  |  |  |  | 128/848 |
| 6,116,580 | A |   | 9/2000 | Hull |  |
| 8,702,569 | B2 | * | 4/2014 | Martin | A63B 23/032 |
|  |  |  |  |  | 482/122 |
| 2008/0201324 | A1 |   | 8/2008 | Aronowich et al. |  |
| 2013/0098372 | A1 | * | 4/2013 | Webster | A61F 5/566 |
|  |  |  |  |  | 128/848 |
| 2014/0238410 | A1 |   | 8/2014 | Goldsby |  |

FOREIGN PATENT DOCUMENTS

EP 3476274 A1 * 5/2019 ............... A61B 1/24

OTHER PUBLICATIONS

Tenda Markets, "Comfort Desk Pro—Adjustable Laptop Stand", Tenda Markets, retrieved from https://www.tendamarkets.co/products/comfort-desk-pro-adjustable-laptop-stand?utm_m . . . , on Oct. 19, 2020, 15 pages.

* cited by examiner

*Primary Examiner* — Tessa M Matthews
*Assistant Examiner* — Tara Rose E Carter
(74) *Attorney, Agent, or Firm* — Foley & Lardner LLP

(57) ABSTRACT

A mouthpiece includes an outer portion comprising a first side, a second side, a first pillar coupled to the first side and configured to rotate about a first axis, a second pillar coupled to the second side and configured to rotate about a second axis, a first upper gum support coupled to the first pillar and configured to rotate about a third axis that is perpendicular to the first axis, a first lower gum support coupled to the first pillar and configured to rotate about a fourth axis that is perpendicular to the first axis, a second upper gum support coupled to the second pillar and configured to rotate about a fifth axis that is perpendicular to the second axis, and a second lower gum support coupled to the second pillar and configured to rotate about a sixth axis that is perpendicular to the second axis.

18 Claims, 23 Drawing Sheets

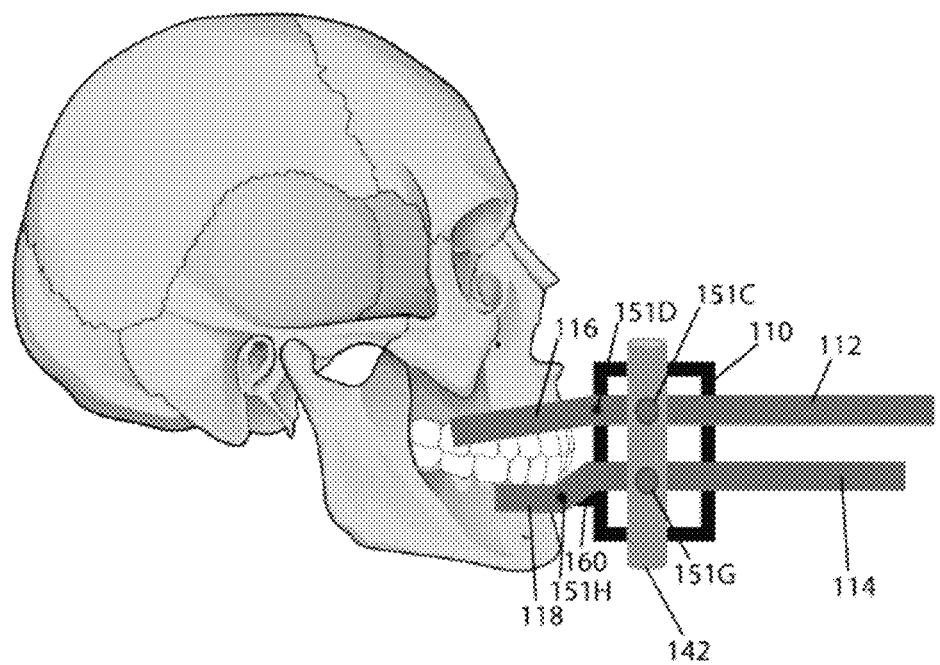
FIG. 3A
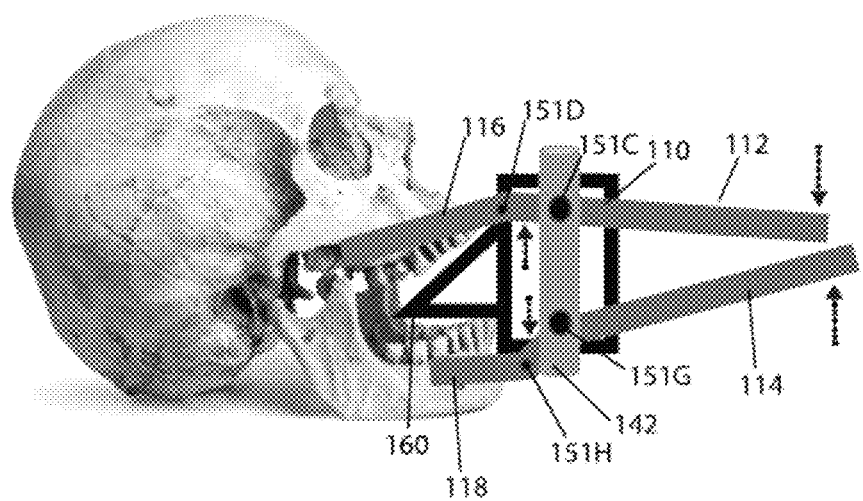
FIG. 3B
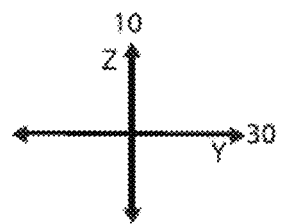

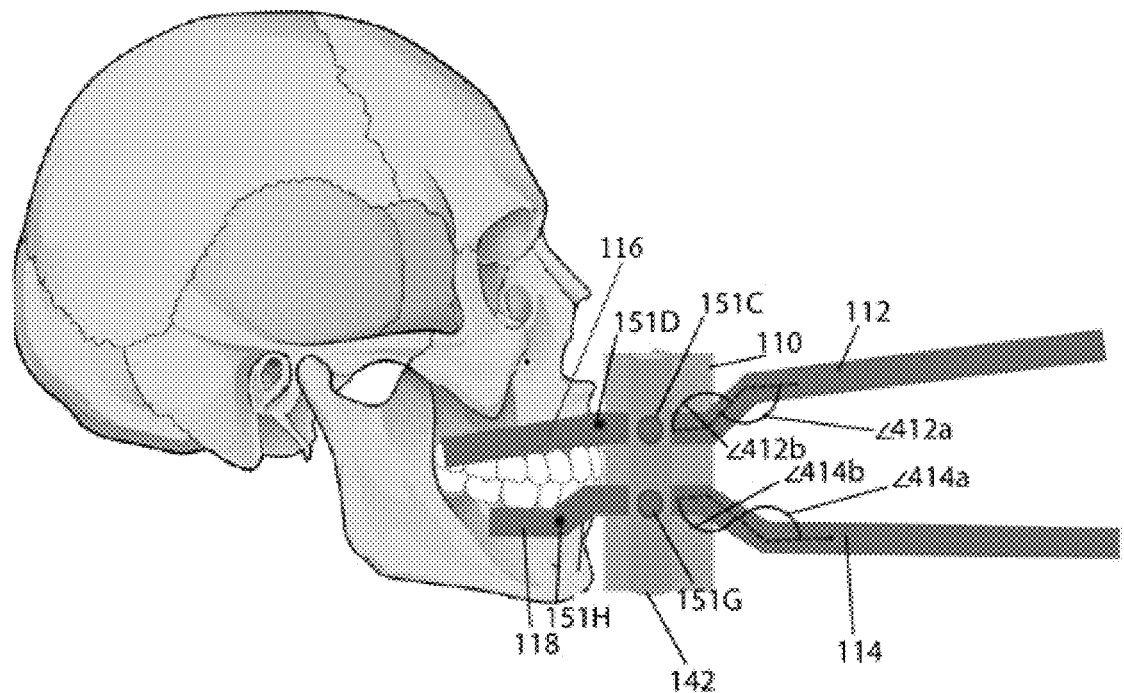
FIG. 4
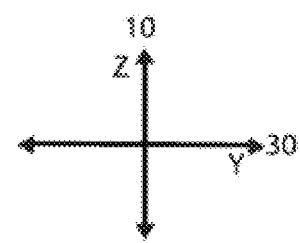

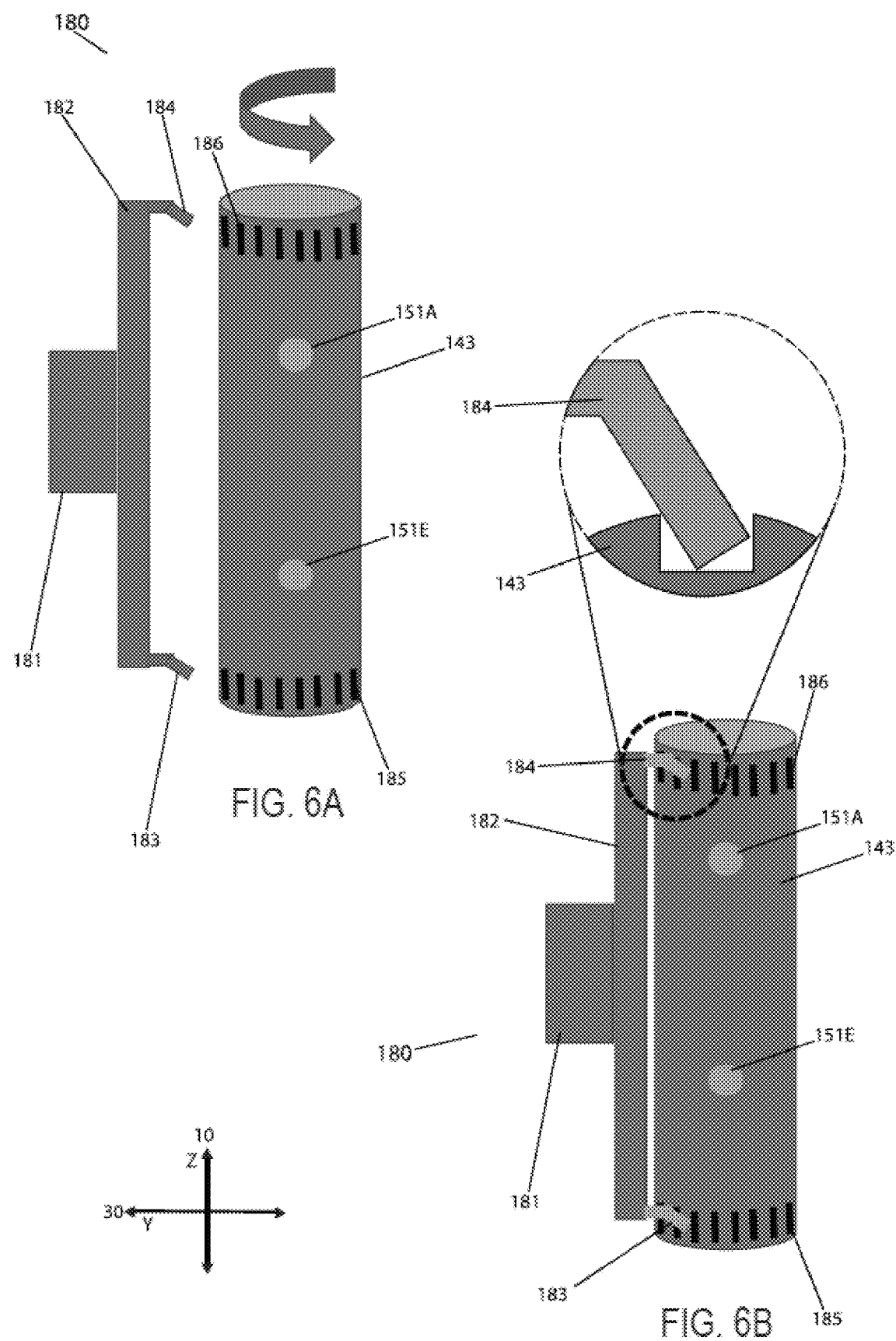

MOUTHPIECE

TECHNICAL FIELD

Embodiments of the present disclosure relate to mouthpieces. More specifically, the present disclosure relates to mouthpieces that can be used to open a patient's mouth and/or keep a patients mouth open (e.g., while intubating a patient, as a part of a medical procedure, etc.).

BACKGROUND

Hospital patients may require use of a breathing tube (i.e., a tracheal tube) in order to assist with the breathing process. For example, hospital patients may not be able to breath on their own due to trauma or an airway complication. Breathing tubes are commonly used when a patient is undergoing general anesthesia during a surgical procedure. Breathing tubes may also be used in emergency situations, such as when the patient is experiencing severe respiratory problems. In use, a breathing tube may be inserted through a patient's mouth and into the trachea, thereby creating a passageway to the patient's lungs to facilitating the exchange of oxygen and carbon dioxide that might otherwise be diminished or prevented.

Hospital patients may further experience a dislocated jaw (e.g., while having a seizure, during a fall, etc.). In this scenario, the jaw may need to be manipulated (e.g., by a medical professional) to return the jaw to the proper position. This may require the medical professional to use his or her hands to forcefully relocate the jaw.

SUMMARY

One embodiment relates to an mouthpiece including an outer portion comprising a first side, a second side, and a lower portion, wherein the lower portion spans between the first side and the second side; a first pillar coupled to the first side and configured to rotate about a first axis; a second pillar coupled to the second side and configured to rotate about a second axis; a first upper gum support coupled to the first pillar and configured to rotate about a third axis that is perpendicular to the first axis; a first lower gum support coupled to the first pillar and configured to rotate about a fourth axis that is perpendicular to the first axis; a second upper gum support coupled to the second pillar and configured to rotate about a fifth axis that is perpendicular to the second axis; and a second lower gum support coupled to the second pillar and configured to rotate about a sixth axis that is perpendicular to the second axis.

According to various embodiments, the mouthpiece further includes an inner wedge configured to be received within the first side and the second side of the outer portion, wherein a lower surface of the inner wedge in configured to be received by the lower portion of the mouth. According to various embodiments, the inner wedge includes an inner primary opening configured to receive a laryngoscope. According to various embodiments, the lower portion includes a curved surface configured to receive a lower portion of a person's face. According to various embodiments, the inner wedge includes a plurality of guide rails configured to be received within a plurality of guide grooves in the outer portion. According to various embodiments, the inner wedge further includes a protrusion extending from an upper surface of the inner wedge, wherein the inner wedge is configured to engage a front portion of a person's mouth. According to various embodiments, the mouthpiece further includes a first sanitary cap coupled to an end of the first upper gum support and configured to receive the first upper gum end; a second sanitary cap coupled to an end of the second upper gum support and configured to receive the second upper gum end; a third sanitary cap coupled to an end of the first lower gum support and configured to receive the first lower gum end; and a fourth sanitary cap coupled to an end of the second lower gum support and configured to receive the second lower gum end.

Another embodiment relates to a mouthpiece including an upper portion configured to receive an upper portion of a person's mouth; a lower portion configured to receive a lower portion of the person's mouth and rotatably coupled to the upper portion such that the mouthpiece is configured to transform between at least an open orientation and a closed orientation; and a locking mechanism coupled to the upper portion and the lower portion, wherein the locking mechanism is configured to prevent the upper portion from rotating relative to the lower portion when the locking mechanism is in a locked orientation, and allow the upper portion to rotate relative to the lower portion when the locking mechanism is in an unlocked orientation.

According to various embodiments, the locking mechanism is configured to transform from the unlocked to the locked orientation in response to a pinching force being applied to the locking mechanism. According to various embodiments, the locking mechanism is configured to transform from the locked orientation to the unlocked orientation in response to experiencing a threshold torsional force. According to various embodiments, the locking mechanisms are positioned proximate a rear portion of the mouthpiece; and the upper portion includes a first tab proximate the front end of the mouthpiece. According to various embodiments, the upper portion includes a second tab proximate the front end of the mouthpiece. According to various embodiments, the locking mechanism is configured to transform from the locked to unlocked position in response to a minimum threshold force being applied to the first tab. According to various embodiments, the locking mechanism includes a first locking components including a plurality of indentations; and a second locking component including a plurality of projections configured to be received by the plurality of indentations when the locking mechanism is in the locked orientation. According to various embodiments, the plurality of projections are positioned outside the plurality of indentations when the locking mechanism is in the unlocked orientation.

Another embodiment relates to a mouthpiece including an upper portion including a front end and a rear end; a lower portion including a front end and a rear end and coupled to the upper portion; and a support member coupled to the lower portion between the front end and the rear end, such that applying a pinching force to the front end of the upper portion and the front end of the lower portion causes the rear end of the upper portion to move away from the rear end of the lower portion.

According to various embodiments, the mouthpiece further includes a first connecting member that couples the rear end of the upper portion to the rear end of the lower portion. According to various embodiments the connecting member includes a spring. According to various embodiments, the mouthpiece further includes a second connecting member that couples the rear end of the upper portion to the rear end of the lower portion. According to various embodiments, the support member is a semi-circular support member with a rounded surface that interfaces with the upper portion.

These and other features, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

FIG. 3A is a side view of the mouthpiece of FIG. 1 in a disengaged position and in relation to a human skull, according to an exemplary embodiment.

FIG. 3B is a side view of the mouthpiece of FIG. 1 in an engaged position and in relation to a human skull, according to an exemplary embodiment.

FIG. 4 is a side view of the mouthpiece of FIG. 1 in a disengaged position and in relation to a human skull, according to an exemplary embodiment.

FIG. 6A is an exploded view of a pillar mechanism of the mouthpiece of FIG. 1, according to an exemplary embodiment.

FIG. 6B is a perspective view of the pillar mechanism of FIG. 6A, according to an exemplary embodiment.

DETAILED DESCRIPTION

Figure 1:
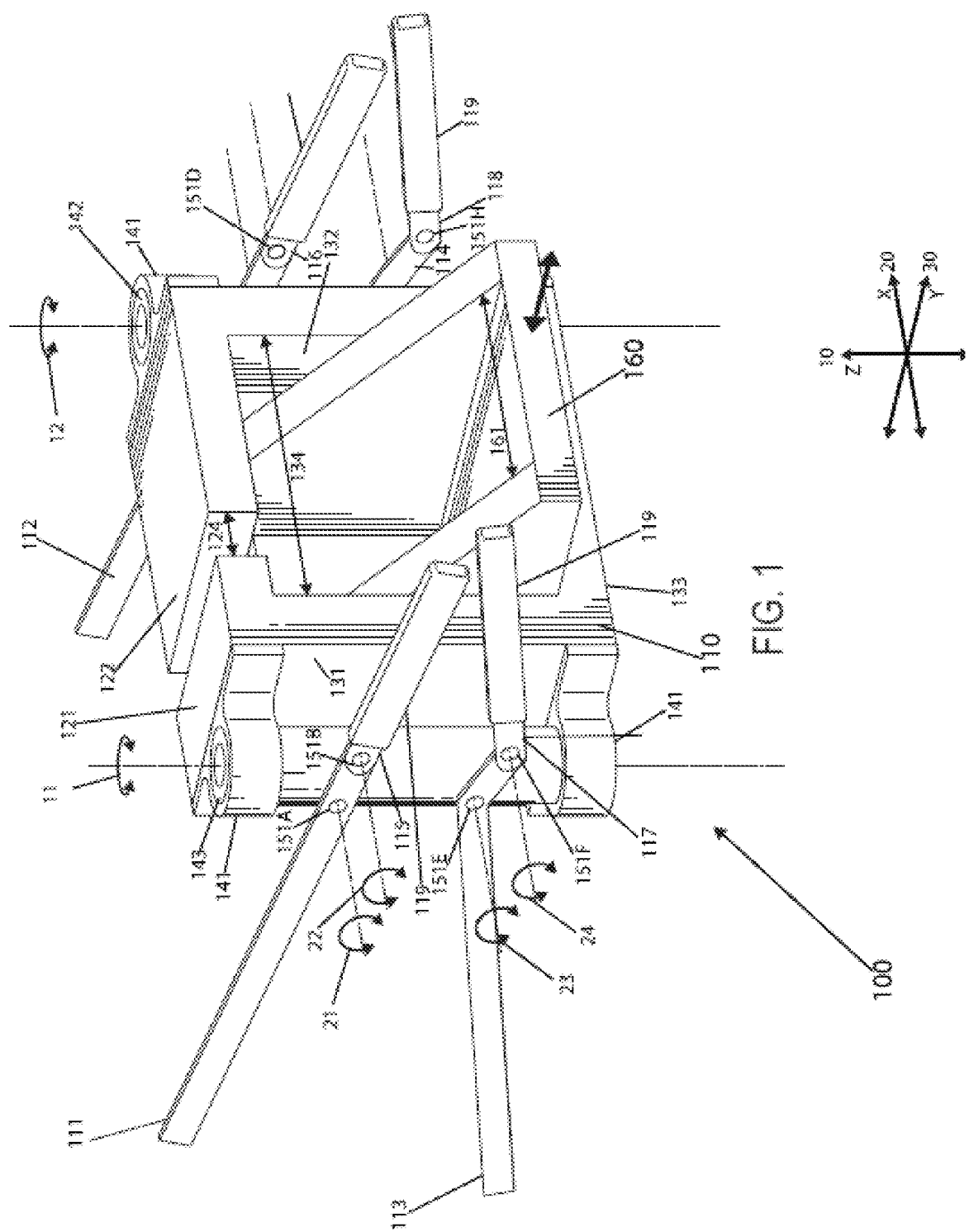
FIG. 1 is a perspective view of a mouthpiece, according to an exemplary embodiment.

The act of inserting the breathing tube into a patient's mouth and into the patient's trachea is referred to as endotracheal intubation. Once the patient is prepared for the endotracheal intubation, which might mean that the patient is unconscious (e.g., due to anesthesia that has been administrated, trauma, etc.) a doctor may use an instrument called a laryngoscope to perform the endotracheal intubation. A laryngoscope is a device that consists of a handle and a dull blade that guides the endotracheal breathing tube to its proper position in the trachea.

Tilting the patient's head back slightly, the doctor will insert the laryngoscope through the patient's mouth and down into their throat. The doctor may need to take special care to avoid the patient's teeth when inserting the laryngoscope. Once the laryngoscope is positioned within in the patient's throat, the doctor may use the laryngoscope's blade to gently raise the patient's epiglottis, which is a flap of tissue that protects the patient's larynx. The doctor may then advance the tip of the endotracheal breathing tube into the patient's trachea, and inflate a small balloon that surrounds the tube to ensure that the tube remains in place. Once the endotracheal breathing tube is properly positioned within the patient, the doctor may remove the laryngoscope and the external portion of the endotracheal breathing tube may be secured (e.g., taped) to the side of the patient's mouth.

In certain situations, patient's mouth may be shut, thereby making it more difficult to insert the endotracheal breathing tube. For example, if a patient is having a seizure (e.g., an epileptic seizure), the patients law may lock (i.e., the patients jaw muscles contract, thereby making it difficult to open the patients mouth). Particularly when a patient is seizing, which can itself be the source of respiratory problems, the muscles around the patient's mouth tighten and prevent their mouth from opening without a great external force. In these cases, it is necessary to provide such an external force but without interacting with the patient's teeth and/or gums directly in order to avoid permanent damage. In this situation, a patient's jaw mat be forcibly opened by the doctor or other individual, however, this may put the safety of the patient and the doctor or other individual in danger. For example, the patient's teeth may be damaged while the patient's jaw is being force opened. Further, the doctor or other individual that is forcing the patient's jaw open may injure their hand and/or fingers while forcibly holding the patient's jaw open.

Referring now to FIGS. 1-12 generally, the mouthpieces disclosed in the present application may be coupled to the patient's jaw and a separating force may be applied to the mouthpiece to creating an opening force to the patient's mouth. For example, the mouthpiece may couple to the outside of the patient's gums. By attaching to a patient's gums, the mouthpiece is not only avoiding contact with sensitive teeth but also reducing the amount of force required to open the patient's jaws, as gums may be more easily manipulated in such a situation. In some embodiments, the mouthpiece is also fitted with a groove or hole that serves to guide an endotracheal breathing tube, enabling the mouthpiece to not only open the patient's mouth but also protect the patient's teeth from further damage as the laryngoscope is inserted into the patient's mouth to guide the breathing tube into place.

In some embodiments, gum separators may be used to couple the mouthpiece to the patient's jaw. For example, the gum separators may be fitted with easily removable caps or sheathes (e.g., sanitary caps) that make contact with the patient's gums. In this embodiment, the caps can be cleaned or disposed of and replaced without much difficulty, ensuring that the device itself can be used repeatedly. The caps may also protect the patient's gums from coming directly in contact with the gum separators, which, in some embodiments, may be made of metal or a similarly rigid material. The caps may be made of any combination of silicone, rubber, and/or any other material approved for use in medical devices, such as ABS, acetal copolymer, delrin, PET-P, flurosint, halar, hydex, kynar, noryl, nylon, PEEK, polycarbonate, polyethlyenes (e.g. LDPE, HDPE, and UHMW), polypropylene homopolymer, PPSU, PSU, radel A, radel R, and Rulon 641.

Referring to FIG. 1, a mouthpiece 100 is shown, according to an example embodiment. As pictured, the mouthpiece 100 includes an outer portion 110 and an inner wedge 160. The inner wedge 160 may be generally wedge shaped. The outer portion 110 may include a first side panel 131, a second side panel 132, a first upper panel 121, a second upper panel 122, and a lower panel 133. As pictured, the first side panel 131 is disposed longitudinally opposite from the second side panel 132 along an x-axis 20. The first upper panel 121 and the second upper panel 122, may be coplanar (e.g. adjacent to laterally, in line with, etc.) within a first plane. The first plane may be parallel to the plane formed by the x-axis 20 and the y axis 30. Further, the first upper panel 121 and the second upper panel 122 may be disposed axially away from the lower panel 133. For example, the lower panel 133 may be positioned lower along a z-axis 10. The surface of the lower panel 133 may form a second plane. In certain embodiments, the second plane is parallel to the first plane.

The outer portion 110 may also include a plurality of pillar supports 141. The pillar supports may be configured to receive a pillar (e.g., a first pillar 143 and a second pillar 142). The first pillar 143 may be fixed to the first side panel 131 by two pillar supports 141 such that the first pillar 143 is oriented along the z-axis 10. The first pillar 143 may be configured to rotate about the z-axis 10, as shown by the arrows 11 in FIG. 1. The second pillar 142 may be fixed to the second side panel 132 by two pillar supports 141 such that the second pillar 142 is oriented along the z-axis 10 and is capable of rotation around the z-axis, as shown by the arrows 12 in FIG. 1.

The outer portion 110 may also include a plurality of gum supports. For example, the outer portion may 110 may include a first upper gum support 111, a second upper gum support 112, a first lower gum support 113, and a second lower gum support 114. In the example embodiment shown, the first upper gum support 111 and the first lower gum support 113 are rotationally fixed to the first pillar 143 via rotator pins 151A and 151E respectively, such that the first upper gum support 111 and the first lower gum support 113 are able to rotate around the rotator pins 151A and 151E respectively, as shown by the arrows 21 and 23 in FIG. 1. The second upper gum support 112 and the second lower gum support 114 may be rotationally fixed to the second pillar 142 via rotator pins 151C and 151H respectively, such that the second upper gum support 112 and the second lower gum support 114 are able to rotate around the rotator pins 151C and 151H respectively.

The first upper gum support 111 extends substantially laterally from the first pillar 143 along a y-axis 30, although the exact angle of extension is variable due to possible rotation by the first pillar 143 and around the rotator pin 151A. The first upper gum support 111 includes a first upper gum end 115 that is rotationally fixed to the first upper gum support 111 by a rotator pin 151B, such that the first upper gum end 115 is able to rotate around the rotator pin 151B, as shown by the arrows 22 in FIG. 1 but otherwise remains in the same alignment with the first upper gum support 111 (i.e. the first upper gum support 111 and the first upper gum end are fixed to each about the other axes). The second upper gum support 112 may be similar to the first upper gum support 111. For example, the second upper gum support 112 extends substantially laterally from the second pillar 142 along the y-axis 30, although the exact angle of extension is variable due to possible rotation by the second pillar 142 and around the rotator pin 151C. The second upper gum support 112 includes a second upper gum end 116 that is rotationally fixed to the second upper gum support 112 by a rotator pin 151D, such that the second upper gum end 116 is able to rotate around the rotator pin 151D, as shown in FIG. 1 but otherwise remains in the same alignment with the second upper gum support 112 (i.e. the second upper gum support 112 and the second upper gum end 116 are fixed to each about the other axes).

In certain embodiments, the first upper gum end 115 is configured to be received by an upper portion of a patient's mouth (e.g., the upper gum line, the upper cheek area, the upper row of teeth, etc.), as is discussed in greater detail below. For example, the first upper gum end 115 may be configured to be received by a first lateral side (e.g., the left side of the patient's mouth) of the upper portion of the patient's mouth. Further, the second upper gum end 116 may be configured to be received by the upper portion of a patient's mouth (e.g., the upper gum line, the upper cheek area, the upper row of teeth, etc.), as is discussed in greater detail below. For example, the second upper gum end 116 may be configured to be received by a second lateral side (e.g., the right side of the patient's mouth) of the upper portion of the patient's mouth. Furthermore, the first lower gum end 117 may be configured to be received by a lower portion of a patient's mouth (e.g., the lower gum line, the lower cheek area, the lower row of teeth, etc.), as is discussed in greater detail below. For example, the first lower gum end 117 may be configured to be received by a first lateral side (e.g., the left side of the patient's mouth) of the lower portion of the patient's mouth. Furthermore, the second lower gum end 118 may be configured to be received by a lower portion of a patient's mouth (e.g., the lower gum line, the lower cheek area, the lower row of teeth, etc.), as is discussed in greater detail below. For example, the second lower gum end 118 may be configured to be received by a second lateral side (e.g., the right side of the patient's mouth) of the lower portion of the patient's mouth.

The first lower gum support 113 extends substantially laterally from the first pillar 143 along a y-axis 30, although the exact angle of extension is variable due to possible rotation by the first pillar 143 and around the rotator pin 151E. The first lower gum support 113 includes a first lower gum end 117 that is rotationally fixed to the first lower gum support 113 by a rotator pin 151F, such that the first lower gum end 117 is able to rotate around the rotator pin 151F, as shown by the arrows 24 in FIG. 1 but otherwise remains in the same alignment with the first lower gum support 113 (i.e. the first lower gum support 113 and the first lower gum end 117 are fixed to each about the other axes). The second lower gum support 114 may be similar to the first lower gum support 113. For example, the second lower gum support 114 extends substantially laterally from the second pillar 142 along the y-axis 30, although the exact angle of extension is variable due to possible rotation by the second pillar 142 and around the rotator pin 151G. The second lower gum support 114 includes a second lower gum end 118 that is rotationally fixed to the second lower gum support 114 by a rotator pin 151H, such that the second lower gum end 118 is able to rotate around the rotator pin 151H, as in FIG. 1 but otherwise remains in the same alignment with the second lower gum support 114 (i.e. the second lower gum support 114 and the second lower gum end 118 are fixed to each about the other axes).

Each of the first upper gum end 115, the first lower gum end 117, the second upper gum end 116, and the second lower gum end 118 (collectively, the gum ends 115-118) include one of a plurality of sanitary caps 119 each of which is removably coupled to the end of the respective the gum ends 115-118 that is opposite of the rotator pin 151. The plurality of sanitary caps 119 are structured to completely cover the tip of the gum ends 115-118 such as to prevent the gum ends 115-118 from making direct contact with the patient. In this way, the plurality of sanitary caps 119 provide a quick and easy method to clean and re-use the mouthpiece 100 between patients. Because the plurality of sanitary caps 119 are the only part of the mouthpiece 100 that makes direct contact with the patient and the plurality of sanitary caps 119 are removably coupled to the gum ends 115-118, every component of the mouthpiece 100 that makes direct contact with the patient is able to be removed and either cleaned or replaced in between uses. Further, the plurality of sanitary caps 119 may be made from a less rigid material than the gum ends, thereby providing a cushion between the gum ends 115-118, which in some embodiments are constructed of a rigid material, and the patient.

In this exemplary embodiment, both the first lower gum support 113 and the second lower gum support 114 include a slight angle immediately prior to the connecting point, which, when combined with the possible rotation of the first lower gum end 117 and the second lower gum end 118 respectively, enables a more ergonomic fit with a patient's mouth by aligning the parts of the mouthpiece 100 that actually make contact to the patient's gums with the natural gum line. In certain embodiments, the slight angle may range between 120-150° as formed by the two portions of the first lower gum support 113 (forming angle <113) and the second lower gum support 114 (forming angle <114) on either side of the rotator pin 151, with the rotator pin 151 defined as a vertex of the angle.

The outer portion 110 may also include an outer primary opening 134 and a secondary opening 124. The primary opening 134 is the space created longitudinally between the first side panel 131 and the second side panel 132 and axially between the first upper panel 121, the second upper panel 122, and the lower panel 133. The secondary opening 124 is the space created longitudinally between the first upper panel 121 and the second upper panel 122. The outer primary opening 134 may be large enough to accommodate a laryngoscope and breathing tube, such that a user doctor has enough space to properly move and manipulate the laryngoscope to ensure proper placement of the breathing tube. The secondary opening 124 is large enough to accommodate the laryngoscope such that the user doctor is able to disengage the laryngoscope from the breathing tube and remove the laryngoscope from the patient's mouth without disrupting the newly-placed breathing tube.

The outer primary opening 134 may be configured to receive the inner wedge 160, such that the inner wedge 160 fits snugly (e.g., the inner wedge 160 is in contact with the outer portion 110) within the outer portion 110. In some embodiments, this snug fit is a friction fit, such that the inner wedge 160 is held in place within the outer portion 110 by the friction force generated by interacting surfaces of the inner wedge 160 and the outer portion 110. The inner wedge 160 is shown in greater detail in FIG. 2, as is discussed below.

Figure 2:
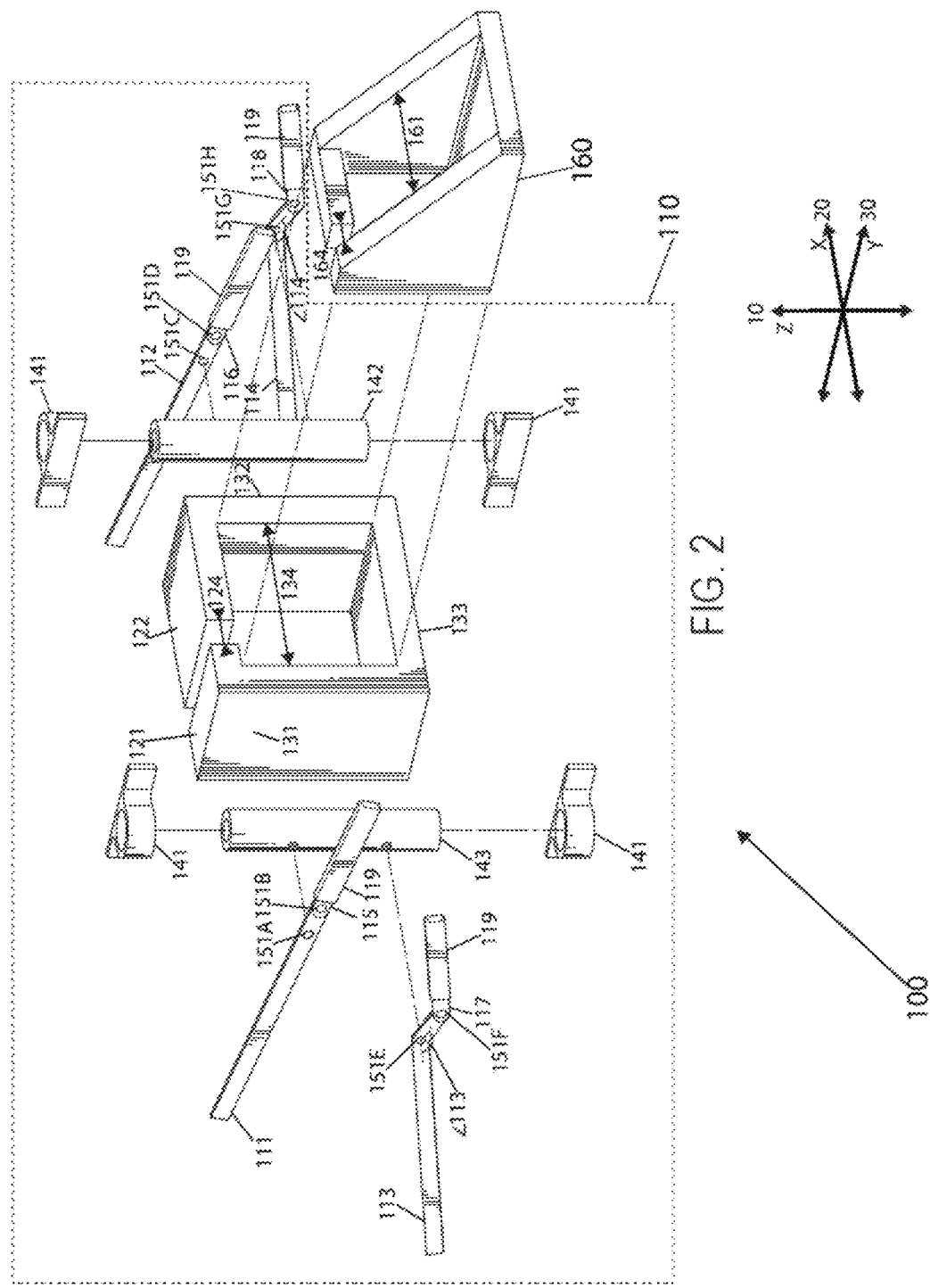
FIG. 2 is an exploded view of the mouthpiece of FIG. 1, according to an exemplary embodiment.
Figure 5A:
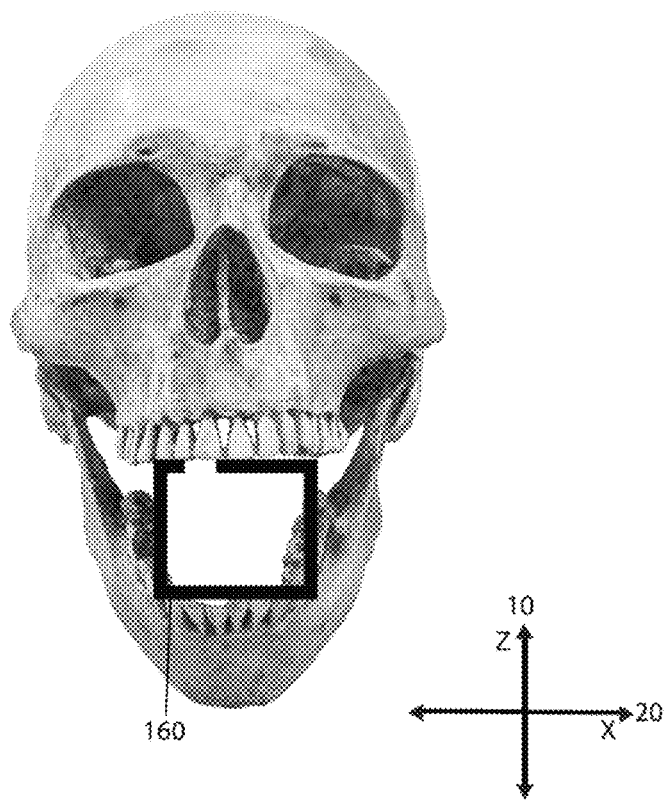
FIG. 5A is a front view of an inner wedge of the mouthpiece of FIG. 1 in relation to a human skull, according to an exemplary embodiment.
Figure 5B:
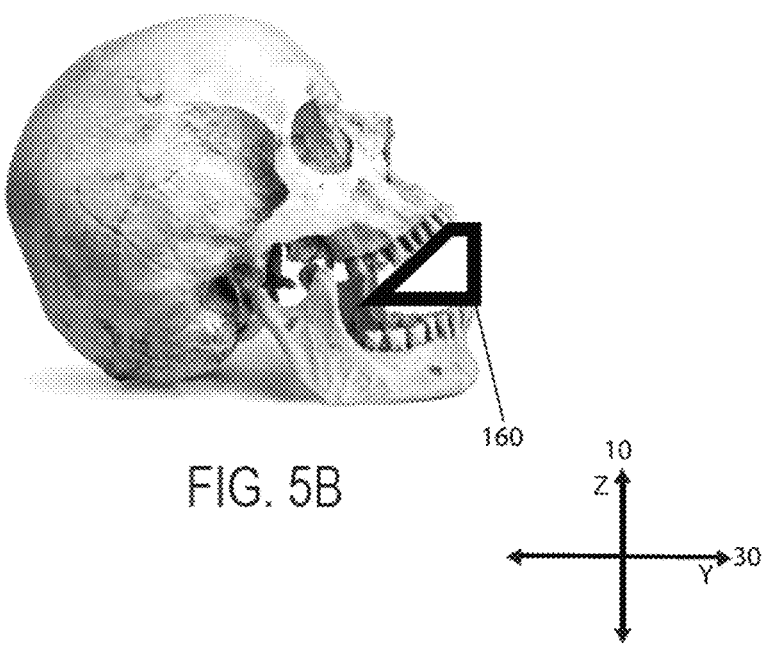
FIG. 5B is a side view of an inner wedge of the mouthpiece of FIG. 1 in relation to a human skull, according to an exemplary embodiment.
Figure 7:
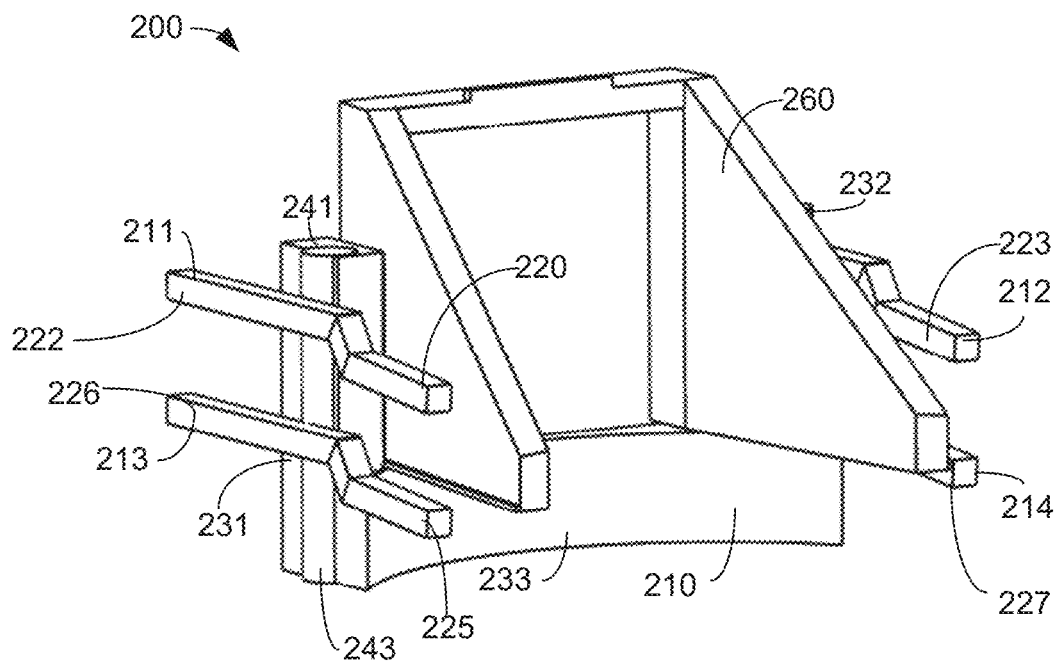
FIG. 7 is a perspective view of a mouthpiece, according to an example embodiment.
Figure 8:
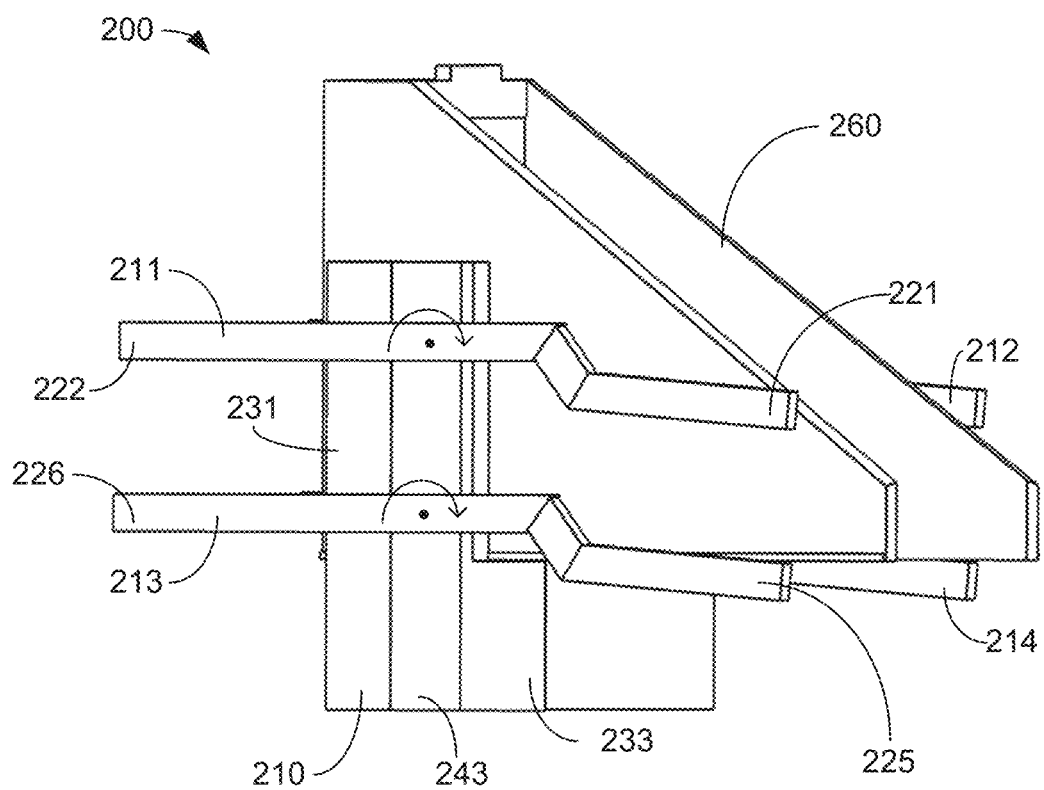
FIG. 8 is another perspective view of the mouthpiece of FIG. 7, according to an example embodiment.
Figure 9:
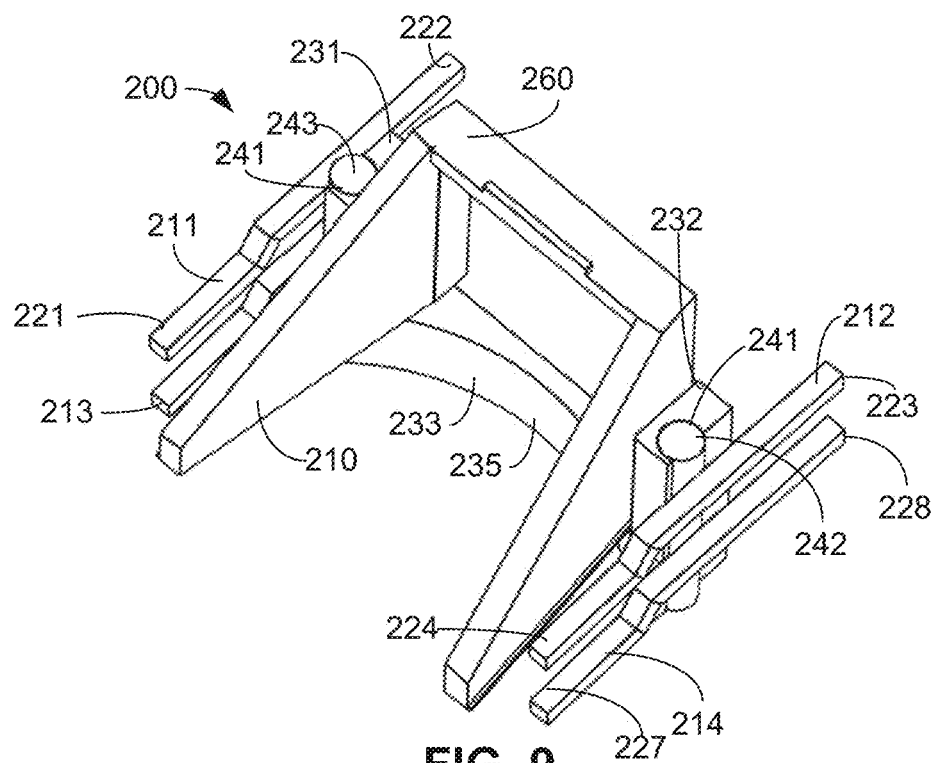
FIG. 9 is another perspective view of the mouthpiece of FIG. 7, according to an example embodiment.

Referring now to FIG. 2, an exploded view of the mouthpiece 100 is shown according to an example embodiment. The mouthpiece 100 may include an inner wedge 160 that includes a wedge secondary opening 164. In certain embodiments, the secondary opening 164 may be the same size as the corresponding secondary opening 124 in the outer portion. The inner wedge 160 may also include an inner primary opening 161. In certain embodiments, the wedge secondary opening 164 may be smaller than the inner primary opening 161. The primary opening 134 may be larger than the outer size of the inner wedge 160. The inner primary opening 161 may be smaller than the primary opening 134 less twice the thickness of the edge sidewalls of the inner wedge 160. In some embodiments, the inner primary opening 161, despite being smaller than the outer primary opening 134, may be large enough to accommodate a laryngoscope and breathing tube, such that a user doctor has enough space to properly move and manipulate the laryngoscope to ensure proper placement of the breathing tube. The inner wedge 160 may be structured to be pushed along the y-axis 30 and into the patient once the separating force has been applied in order to prop the patient's jaw open, enabling removal of the outer portion 110 without causing the object to return to its prior closed state in which air flow was restricted.

In use, the mouthpiece 100 may be used to create a separating force (e.g., an opening force) to open a patient's jaw. For example, a doctor or other user of the mouthpiece 100 may use the first upper gum support 111, the second upper gum support 112, the first lower gum support 113, and the second lower gum support 114 (collectively, the gum supports 111-114) to create the separating force. In an example embodiment, the gum supports 111-114 are fit to the object requiring the separating force (e.g., the patient's gums, mouth, teeth, jaw, cheeks, etc.). The gum supports 111-114 may be adjusted to fit a specific patient by rotating the gum supports 111-114 about the rotator pins 151 connected to the first pillar 143 and the second pillar 142 and rotating the gum ends 115-118 about the plurality of rotator pins 151 connected to the gum supports 111-114. Once the gum supports 111-114 are in a desired orientation, the gum supports 111-114 are tightened onto the objecting requiring the separating force (e.g., the patient's gums, mouth, teeth, jaw, cheeks, etc.) by rotating the first pillar 143 and the second pillar 142 in the plurality of pillar supports 141. Once tightened, a compressing force along the z-axis 10 is applied to the ends of the first upper gum support 111 and the first lower gum support 113 opposite the plurality of sanitary caps 119, and a compressing force along the z-axis 10 is applied to ends of the second upper gum support 112 and the second lower gum support 114 that are opposite the plurality of sanitary caps 119. For example, a compressing force may be applied by a doctor or other operator of the mouthpiece 100. Further, the mouthpiece 100 may be connected to a motor, or multiple motors, that may creating a compressing force. When the compressing forces are applied, the plurality of sanitary caps 119 move in the opposite direction of the compressing forces along the z-axis 10, such that the separating force is applied to the desired object and airflow through the object is enabled.

Referring now to FIGS. 3A and 3B, the mouthpiece 100 is shown according to an example embodiment. In this exemplary embodiment, the object is a human skull. As shown in FIG. 3A, the mouthpiece 100 is shown interacting with the human skull via the second upper gum end 116 and the second lower gum end 118 in contact with the human skull directly above a top row of teeth and below a bottom row of teeth, respectively. The second upper gum end 116 and the second lower gum end 118 may be rotated around the rotator pins 151D and 151H respectively in order to be properly positioned on the gum lines of the human skull. Although not shown in FIG. 3A, any action performed on or function performed by the second upper gum end 116 and the second lower gum end 118 may also be performed on or by the first upper gum end 115 and the first lower gum end 117 respectively. As such, the second upper gum end 116 and the second lower gum end 118 interact with the human skull at a gum line of the human skull. Once the second upper gum end 116 and the second lower gum end 118 are in place, the rotating force around the second pillar 142 is applied to the second upper gum support 112 and the second lower gum support 114, tightening the second upper gum end 116 and the second lower gum end 118 onto the gum line of the human skull.

It should be appreciated that, in certain embodiments, the first upper gum support 111 and the first upper gum end 115 may be one rigidly fixed piece (i.e., the first upper gum support 111 is not rotatably fixed to the first upper gum end 115, but is instead rotatably fixed to the first upper gum end 115). For example, the first upper gum support 111 and the first upper gum end 115 may be manufactured as a single. Further, the second upper gum support 112 and the second upper gum end 116 may be one rigidly fixed piece. Furthermore, the first lower gum support 113 and the first lower gum end 117 may be one rigidly fixed piece. Furthermore, the second lower gum support 114 and the second lower gum end 118 may be one rigidly fixed piece.

As shown in FIG. 3B, the mouthpiece 100 may be manipulated such that the mouthpiece 100 is in an enabled position following application of the separating force. As shown, one end of the second upper gum support 112 and one end of second lower gum support 114 are moved closer together along the z-axis 10 (as shown by dashed arrows). Rotation of the second upper gum support 112 and the second lower gum support 114 around the rotator pins 151C and 151G moves the opposite ends of the second upper gum support 112 and the second lower gum support 114 apart along the z-axis 10 (as shown by the dashed arrows), which, in turn, separates the second upper gum end 116 and the second lower gum end 118 along the z-axis 10. Because the second upper gum end 116 and the second lower gum end 118 are tightly fit to the gum lines of the human skull, the separating force applied to the second upper gum end 116 and the second lower gum end 118 is transferred in equal quantity to the human skull, thereby separating a lower jaw of the human skull from an upper jaw of the human skull, along the z-axis 10. Once the jaws have been separated, the inner wedge 160 may be pushed from a receded position shown in FIG. 3A into the space between the upper jaw and the lower jaw as shown in FIG. 3B.

Referring now to FIG. 4, the mouthpiece 100 is shown in a disengaged orientation according to another example embodiment. As shown in FIG. 4, in some embodiments, both the second upper gum support 112 and the second lower gum support 114 include a set of slight angles prior to the connecting point with the second pillar 142, which enables a more ergonomic fit for an operating user (e.g., a doctor, nurse, etc.) by giving more room for the separating force to be applied to the gum supports 111-114. In certain embodiments, the set of slight angles includes two separate angles for each gum support 111-114: as shown in FIG. 4, the second upper gum support 112 includes angles <412A and <412B, while the second lower gum support 114 includes angles <414A and <414B. In certain embodiments, angles <412A-B and <414A-B may range from 120-150° formed by portions of the second upper gum support 112 (forming angles <412A-B) and the second lower gum support 114 (forming angles <414A-B).

In some of these embodiments, the gum ends 115-118 make direct contact with the gum lines of the human skull. In other of these embodiments, each of the gum ends 115-118 includes at least one of the plurality of sanitary caps 119, such that the plurality of sanitary caps are the only components of the mouthpiece in direct contact with the human skull. In these embodiments with the plurality of sanitary caps 119, the sanitary caps are removably coupled to an end of the gum ends 115-118 as shown in FIGS. 1 and 2.

In some embodiments, once the inner wedge 160 is in position (i.e. between the upper jaw and the lower jaw), the second upper gum end 116 and the second lower gum end 118 are loosened from the gum lines of the human skull (a process described in greater depth below). Because the second upper gum end 116 and the second lower gum end 118 are no longer in contact with the gum lines of the human skull, the separating force being transferred to the human skull via the second upper gum end 116 and the second lower gum end 118 are no longer transferred. As such, the upper jaw and the lower jaw may rest on the inner wedge 160 (i.e., the upper angled surface of the inner wedge may be in contact with the upper portion of the patient's mouth and the lower flat surface may be in contact with the lower portion of the patient's mouth), thereby keeping the jaw in an open orientation. In some of these embodiments, the outer portion 110 may then be removed, which is discussed in greater detail in FIGS. 5A and 5B.

Once the mouthpiece 100 is positioned within a desired location, an operator of the mouthpiece may secure the gum supports 111-114 to prevent the gum supports 111-114 from undesirably shifting. For example, in some embodiments, the gum supports 111-114 and associated components are restricted in movement because the rotator pins 151, the first pillar 143, the second pillar 142, and the plurality of pillar supports 141 are structured such that the force required to cause rotation of the first pillar 143 or the second pillar 142 or rotation of any component around the rotator pins 151 (i.e. inertia) is greater than is supplied by the natural resistance (i.e. friction) of the object upon which the separating force is being applied. Put differently, the components of the mouthpiece 100, in these embodiments, are so tightly fixed as to be adjusted only by a directed applied force and not by accidental force.

In another embodiment, the first pillar 143, the second pillar 142, and the plurality of pillar supports 141 are structured such that the first pillar 143 and the second pillar 142 are only capable of unhindered rotation in a single direction. This may be accomplished via a pillar mechanism 180. The pillar mechanism 180 is shown in greater detail in FIGS. 6A-B. Although FIGS. 6A-B only show the pillar mechanism 180 in relation to the first pillar 143, any disclosure herein should not be restricted to the first pillar 143 and should be read as equally applicable to the second pillar 142. As shown in FIG. 6A, the pillar mechanism 6A includes a mechanism bar 182, a release tab 181, an upper tab 184, and a lower tab 183. The mechanism bar 182 extends axially along the z-axis 10 and is substantially parallel to the first pillar 143. The mechanism bar 182 includes the upper tab 184 on one end and the lower tab 183 on the other end, relative to the z-axis 10. The release tab 181 extends perpendicularly from the mechanism bar 182.

The pillar mechanism 180 may be manipulated between an engaged mode and a disengaged mode. When the pillar mechanism 180 is in the engaged mode, the first pillar 143 is only able to rotate in a first direction, such that the first pillar 143 is prevented from rotating in a second direction. In the example embodiment shown in FIGS. 6A-B, the first direction is counter clock-wise around the z-axis 10, and the second direction is clock-wise around the z-axis 10. In other words, when the pillar mechanism is in the engaged mode, the first pillar 143 is only able to rotate in the direction indicated by the arrow in FIGS. 6A-B. When the pillar mechanism 180 is in the disengaged mode, the rotation ability of the first pillar 143 is not restricted such that the first pillar 143 can rotate in either the first direction or the second direction. However, regardless of the mode of the pillar mechanism 180, the first pillar 143 is restricted in lateral or longitudinal movement by the plurality of pillar supports 141.

The pillar mechanism 180 may be manipulated from the engaged mode to the disengaged mode via the release tab 181. By default (i.e., when the release tab 181 is not pressed), the pillar mechanism 180 is in the engaged mode due to a spring (not shown). In the engaged mode, the upper tab 184 and the lower tab 183 interact with a plurality of grooves on the first pillar 143. This interaction is shown (for the upper tab 184) in the blown-up portion of FIG. 6B. When the release tab 181 is pressed, the upper tab 184 and the lower tab 183 move perpendicularly away from the first pillar 143 such that the upper tab 184 and the lower tab 183 no longer interact with the plurality of grooves in the first pillar 143.

In certain embodiments, the gum supports 111-114 and the gum ends 115-118 are manipulated and adjusted until in the desired position, at which point the first pillar 143 and the second pillar 142 are rotated in the first direction until the plurality of sanitary caps 119 are snugly fit on the object (e.g., gums of a human patient). Then, due to the restrictions placed by the pillar mechanism 180, the first pillar 143 and the second pillar 142 are held in place, and the fit of the sanitary caps 119 on the object remains snug. Once the related activity is completed (e.g., the separating force is no longer desired), the release tab 181 is pressed and the first pillar 143 and the second pillar 142 are free to rotate, thereby releasing the snug fit of the plurality of sanitary caps on the object.

Referring now to FIGS. 7-10, a mouthpiece 200 is shown, according to an example embodiment. The mouthpiece 200 may be similar to the mouthpiece 100 and may provide similar functionality as the mouthpiece 100. For example, the mouthpiece 200 may be used to open a person's mouth while also protecting the patient's teeth from further damage as a laryngoscope is inserted into the patient's mouth to guide a breathing tube into place in a similar manner as the mouthpiece 200.

As shown, the mouthpiece 200 includes an outer portion 210 and an inner portion 260 (e.g., inner wedge). As shown, the inner portion 260 (e.g., inner wedge) is generally wedge shaped. The outer portion 210 includes a first side 231, a second side 232 opposite the first side, and a lower portion 233 that connects the first side 231 to the second side 232. As pictured, the first side 231 is disposed longitudinally opposite from the second side 232. According to various embodiments, the first side 231 is a mirror image of the second side 232, such that the first side 231 and the second side 232 may enable similar functionality, as will be discussed further below. As shown, the lower portion 233 includes a rounded surface 235. The rounded surface 235 is configured to receive a portion of a person's head and neck area (e.g., the chin), as will be discussed further below.

The outer portion 210 also include a plurality of pillar supports 241. As shown, the pillar supports 241 are configured to receive a pillar (e.g., a first pillar 243 and a second pillar 242), such that the pillar may rotate within the pillar support 241 about an axis of rotation (e.g., a first axis 201 or a second axis 203, shown in FIG. 10). According to various embodiments, the amount of rotation of each pillar may be limited by the first side 231 and the second side 232. For example, the outer portion may 210 may include a first upper gum support 211, a second upper gum support 212, a first lower gum support 213, and a second lower gum support 214 that are each coupled to the pillar. As the pillar rotates, one or more gum supports may interface with the first side 231 or the second side 232 thereby preventing further rotation of the pillar.

Figure 10:
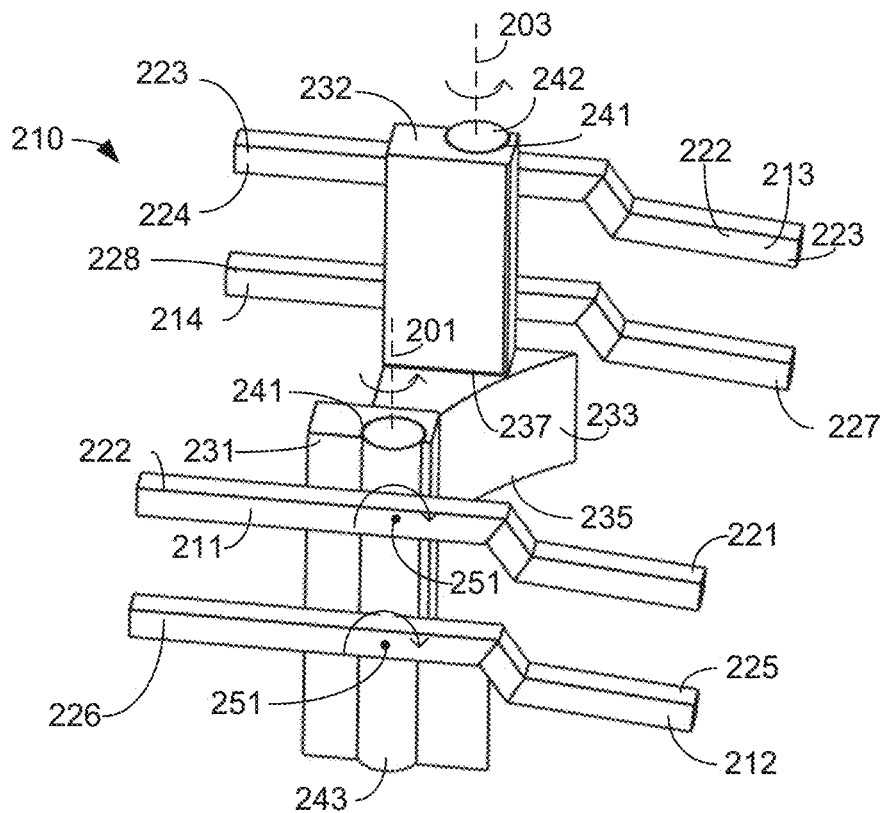
FIG. 10 is a perspective view of the outer portion of the mouthpiece of FIG. 7, according to an example embodiment.

In the example embodiment shown, the first upper gum support 211 and the first lower gum support 213 are rotationally fixed to the first pillar 243, such that the first upper gum support 211 and the first lower gum support 213 are able to rotate about a point of rotation 251, as shown by the arrows in FIG. 10. Similarly, the second upper gum support 212 and the second lower gum support 214 are rotationally fixed to the second pillar 242, such that the second upper gum support 212 and the second lower gum support 214 are able to rotate about the second pillar 242.

The first upper gum support 211 extends substantially laterally from the first pillar 243, although the exact angle of extension may be variable due to possible rotation by the first pillar 243. The first upper gum support 211 includes a first end 221 and a second end 222 opposite the first end 221. The first end 221 is configured to be received within an upper portion of a patient's mouth (e.g., the upper gum line, the upper cheek area, the upper row of teeth, etc.). The second end 222 is configured to receive a force (e.g., a medical professional applying a downward force to the second end 222). The force may cause the first upper gum support 211 to rotate (e.g., about the point of rotation 251), thereby causing the first end 221 to move in the opposite direction of the second end 222.

The second upper gum support 212 includes a first end 223 and a second end 224 opposite the first end 223. The first end 223 is configured to be received within an upper portion of a patient's mouth (e.g., the upper gum line, the upper cheek area, the upper row of teeth, etc.). The second end 224 is configured to receive a force (e.g., a medical professional applying a downward force to the second end 224). The applied force may cause the second upper gum support 212 to rotate (e.g., about the point of rotation 251), thereby causing the first end 223 to move in the opposite direction of the second end 224.

The first lower gum support 213 includes a first end 225 and a second end 226 opposite the first end 225. The first end 225 is configured to be received within a lower portion of a patient's mouth (e.g., the lower gum line, the lower cheek area, the lower row of teeth, etc.). The second end 226 is configured to receive a force (e.g., a medical professional applying a downward force to the second end 226). The applied force may cause the first lower gum support 213 to rotate (e.g., about the point of rotation 251), thereby causing the first end 225 to move in the opposite direction of the second end 226.

The second lower gum support 214 includes a first end 227 and a second end 228 opposite the first end 227. The first end 227 is configured to be received within a lower portion of a patient's mouth (e.g., the lower gum line, the lower cheek area, the lower row of teeth, etc.). The second end 228 is configured to receive a force (e.g., a medical professional applying a downward force to the second end 228). The applied force may cause the second lower gum support 214 to rotate (e.g., about the point of rotation 251), thereby causing the first end 227 to move in the opposite direction of the second end 228.

According to various embodiments, each of the first ends 221, 223, 225, 227 (collectively, the gum ends 221, 223, 225, 227) include one of a plurality of sanitary caps, which may be removably coupled to the end of the respective the gum ends 221, 223, 225, 227. The plurality of sanitary caps may be the same or similar to the sanitary caps 119 described above.

In this exemplary embodiment, both the gum supports 211, 212, 213, 214 include a slight bend between the axis of rotation and the gum ends 221, 223, 225, 227. The slight bend may enable a more ergonomic fit with a patient's mouth by aligning the parts of the mouthpiece 200 that actually make contact to the patient's gums with the natural gum line. In certain embodiments, the slight angle may range between 120-150°.

The outer portion 210 further includes an opening between the first side 231 and the second side 232. The opening is configured to receive the inner portion 260. For example, the gum supports 211, 212, 213, 214 may be used to open a person's mouth, and the inner portion 260 may translate within the opening such that the inner portion 260 is inserted into the person's open mouth, as is discussed further below. According to various embodiments, the opening is large enough to accommodate the laryngoscope such that the user doctor is able to disengage the laryngoscope from the breathing tube and remove the laryngoscope from the patient's mouth without disrupting the newly-placed breathing tube. According to various embodiments, the opening may also include a pair of guide grooves 237 that are configured to receive a pair of guide rails 270, 272, as is discussed further below with respect to FIGS. 11 and 12.

Figure 11:
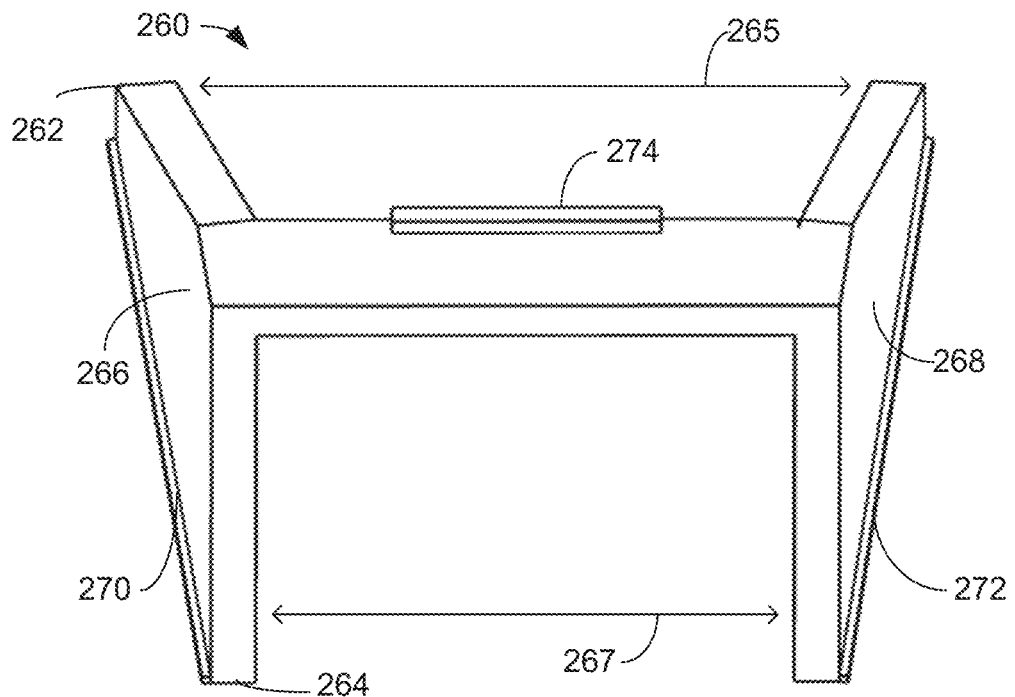
FIG. 11 is a perspective view of the inner portion of the mouthpiece of FIG. 7, according to an example embodiment.
Figure 12:
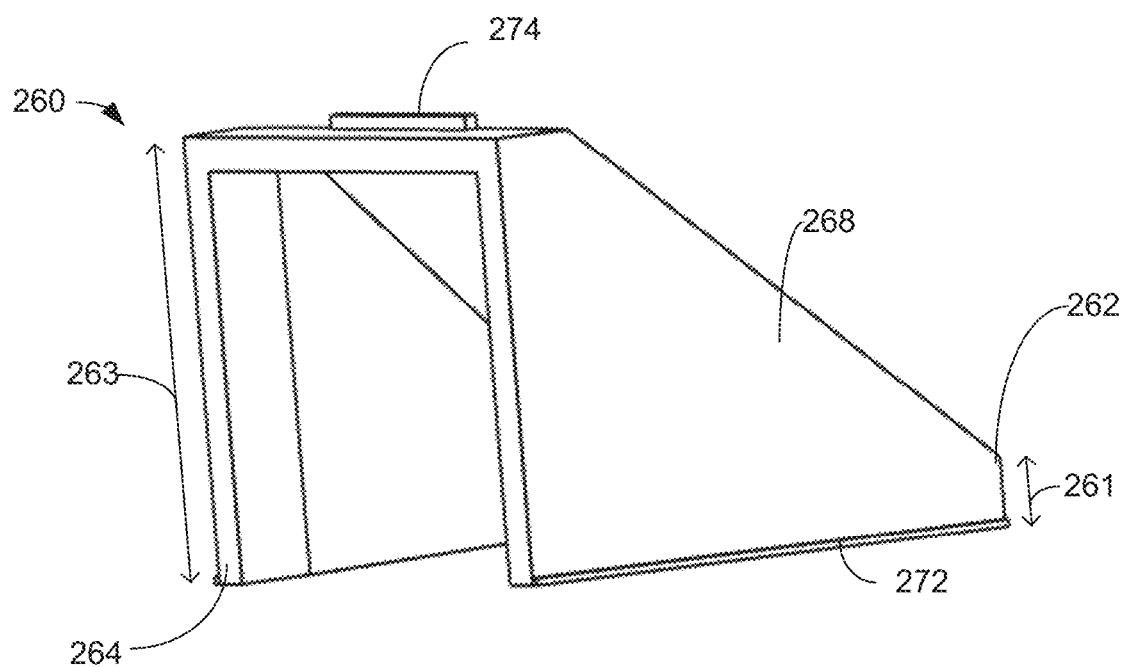
FIG. 12 is another perspective view of the inner portion of the mouthpiece of FIG. 7, according to an example embodiment.

Referring now to FIGS. 11 and 12, the inner portion 260 is shown in greater detail. As shown, the inner portion 260 is generally wedge shaped. As a result, the height 261 proximate a first end 262 of the inner portion 260 is less than the height 263 proximate a second end 264 of the inner portion 260. In this sense, when the first end 262 is positioned within a person's mouth and the inner portion 260 is further inserted into the mouth, the upper portion of the mouth will be forced away from the lower portion of the mouth, as is discussed further below.

The inner portion 260 further includes a first leg 266 and a second leg 268 that extend between the first end 262 and the second end 264. As shown in FIG. 11, the first leg 266 and the second leg 268 are angled such that an opening 265 proximate the first end 262 is wider than an opening 267 proximate the second end 264. According to various embodiments, the angle of the legs may provide a more ergonomic fit within a person's mouth. Further, the first leg 266 and the second leg 268 are shown to include a first guide rail 270 and a second guide rail 272, respectively. The guide rails 270, 272 are configured to be revived by the guide grooves 237 (see FIG. 10), such that a portion of the guide rails 270, 272 translate within the guide grooves 237 while the inner portion 260 translates within the outer portion 210, thereby providing additional stability.

The inner portion 260 further includes a protrusion 274 extending from an upper surface of the inner portion 260. According to various embodiments, the protrusion 274 is configured to interface with an upper part of a person's mouth area (e.g., the upper teeth, upper lip, etc.) such that the protrusion 274 may prevent the inner portion 260 from being overly inserted into the person's mouth as the inner portion 260 is inserted to open the person's mouth.

Figure 13:
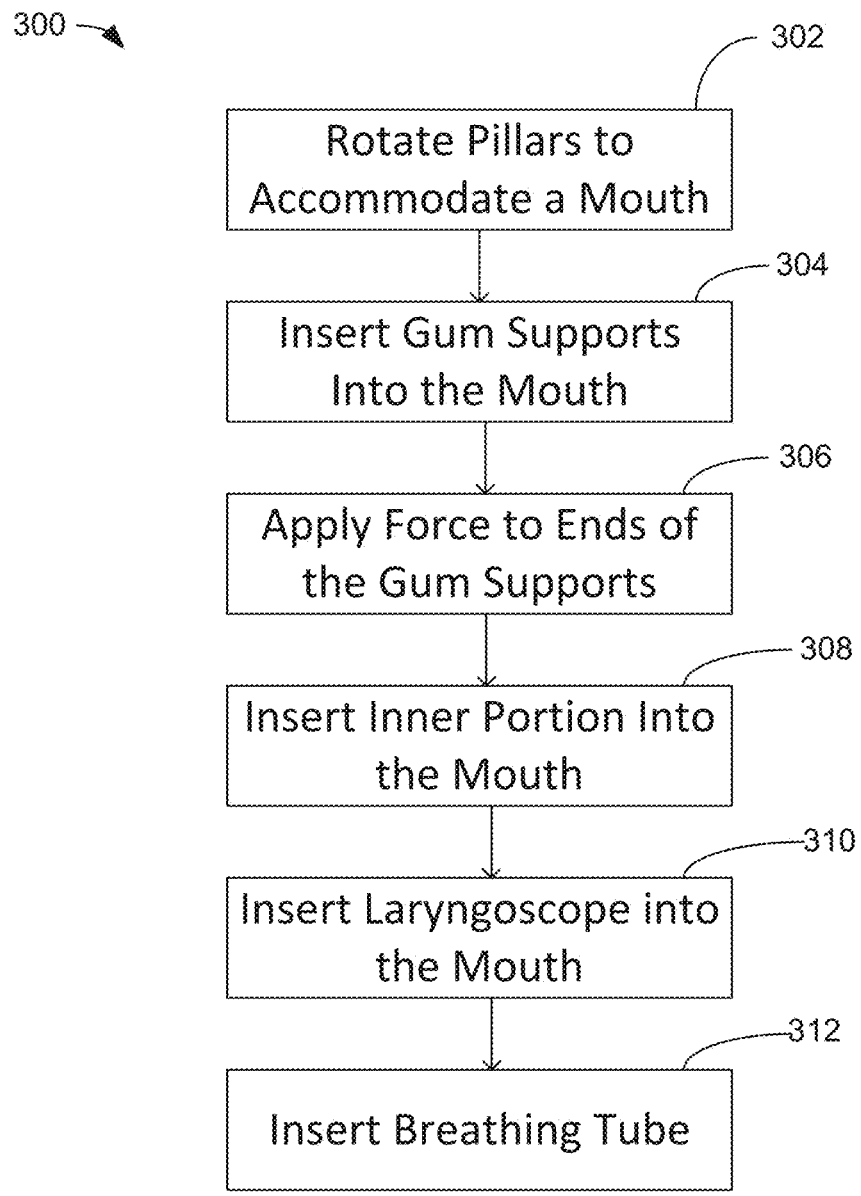
FIG. 13 is a block diagram of an intubation process, according to an example embodiment.

Referring now to FIG. 13, a block diagram of an intubation process 300 is shown, according to an example embodiment. The process 300 contemplates using some or all of the mouthpieces (e.g., the mouthpiece 100, the mouthpiece 200, the mouthpiece 400, etc.) described herein. The process 300 may be used, for example, to intubate a person experiencing a seizure. It should be appreciated that the process 300 need not be performed in the order shown, certain process may be omitted, and additional processes may be included.

As shown, process 300 includes process 302, which involves rotating pillars (e.g., the first pillar 243, the second pillar 242, etc.) to accommodate a mouth. For example, the pillars may be rotated to align with the contours of the person's mouth. Once the pillars are rotated into the desired position, the gum supports (e.g., gum supports 211, 212, 213, 213) may be inserted into the person's mouth as a part of process 304. For example, upper gum supports may be inserted into the upper portion of the person's mouth and lower gum supports may be inserted into the lower portion of the person's mouth. As a part of process 304, a portion of the mouthpiece (e.g., the rounded surface 235) may interface with a portion of the person's face (e.g., the chin area) to stabilize the mouthpiece.

Once the gum supports are in the desired position within the person's mouth, a force may be applied to the ends (e.g., the second ends 222, 224, 226, 228) of the gum supports as a part of process 306. Applying the force (e.g., a clamping force) to the ends of the gum supports that are not positioned within the person's mouth may then cause the ends of the gum supports positioned within the person's mouth to move away from each other, thereby applying a separating force (e.g., an opening force) to open the person's jaw. This separating force may cause the person's mouth to open wide enough to accommodate an end (e.g., the first end 262) of an inner portion (e.g., the inner portion 260) of the mouthpiece.

At process 308, the inner portion is inserted into the person's mouth. As is discussed above, the wedge shape of the inner portion may cause the mouth to open wider as the inner portion is further inserted into the person's mouth. The inner portion may be inserted until the mouth is opened wide enough to receive a Laryngoscope. At process 310, a Laryngoscope is inserted into the person's mouth. For example, the Laryngoscope me the inserted through an opening in the inner portion (e.g., the openings 265, 267) while the inner portion is still at least partially positioned within the person's mouth. Once the Laryngoscope is inserted into the person's mouth and positioned in a desired location, a breathing tube may be inserted into the patient's throat as a part of process 312.

Figure 14A:
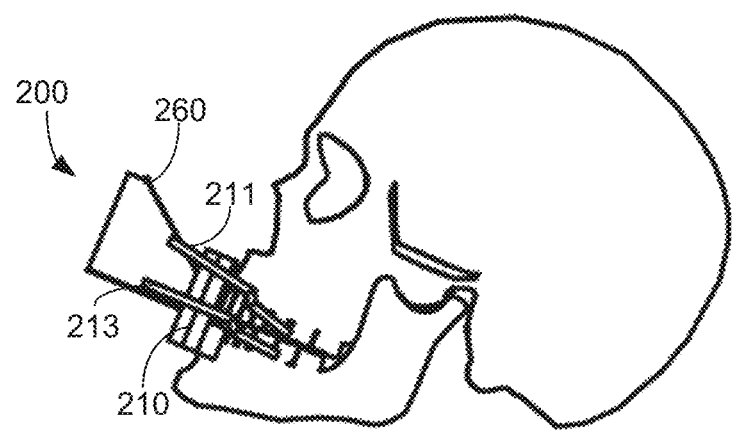
FIGS. 14A-C are visual representations of the mouthpiece of FIG. 7 being used to open a person's mouth, according to an example embodiment.
Figure 14B:
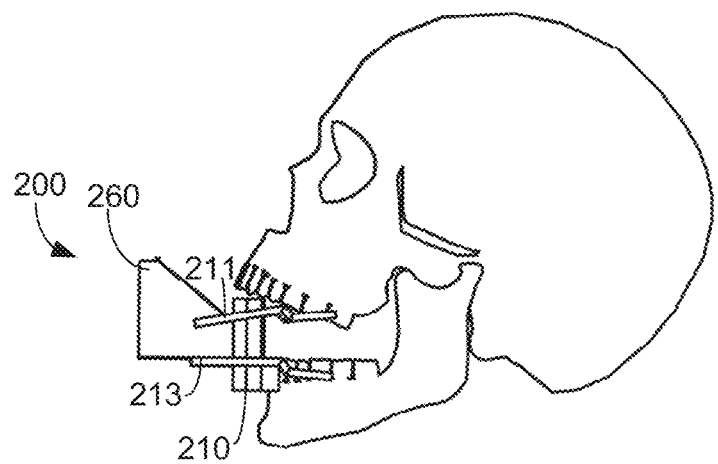
Figure 14C:
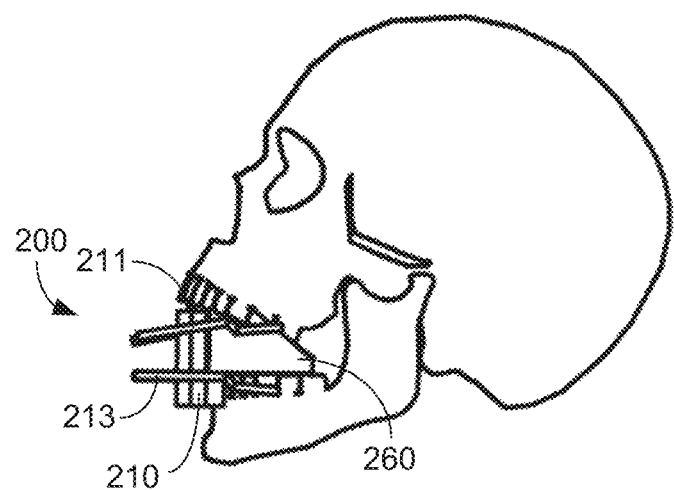

Referring now to FIGS. 14A-14C, a visual representation of the mouthpiece 200 being used to open a person's mouth is shown, according to an example embodiment. For example, FIG. 14A may correspond with process 304, FIG. 14B may correspond with process 306, and FIG. 14C may correspond with process 306. As shown in FIG. 14A, the gum supports (e.g., gum supports 211, 213) are inserted into the patients mouth. For example, the gum supports may interface with the person's teeth and/or gum area. As shown in FIG. 14B, a force is applied to the ends of the gum supports that are not positioned within the person's mouth, thereby applying an opening force to the persons mouth. As shown in FIG. 14C, the inner portion 260 is pushed into the person's mouth, thereby further opening the persons mouth and keeping the mouth open such that a Laryngoscope may be inserted into the person's mouth while the inner portion 260 is at least partially positioned within the person's mouth.

It should be appreciated that some or all of the components of the mouthpiece 200 may be made of any combination of silicone, rubber, and/or any other material approved for use in medical devices, such as ABS, acetal copolymer, delrin, PET-P, flurosint, halar, hydex, kynar, noryl, nylon, PEEK, polycarbonate, polyethlyenes (e.g. LDPE, HDPE, and URMW), polypropylene homopolymer, PPSU, PSU, radel A, radel R, and Rulon 641.

Figure 15:
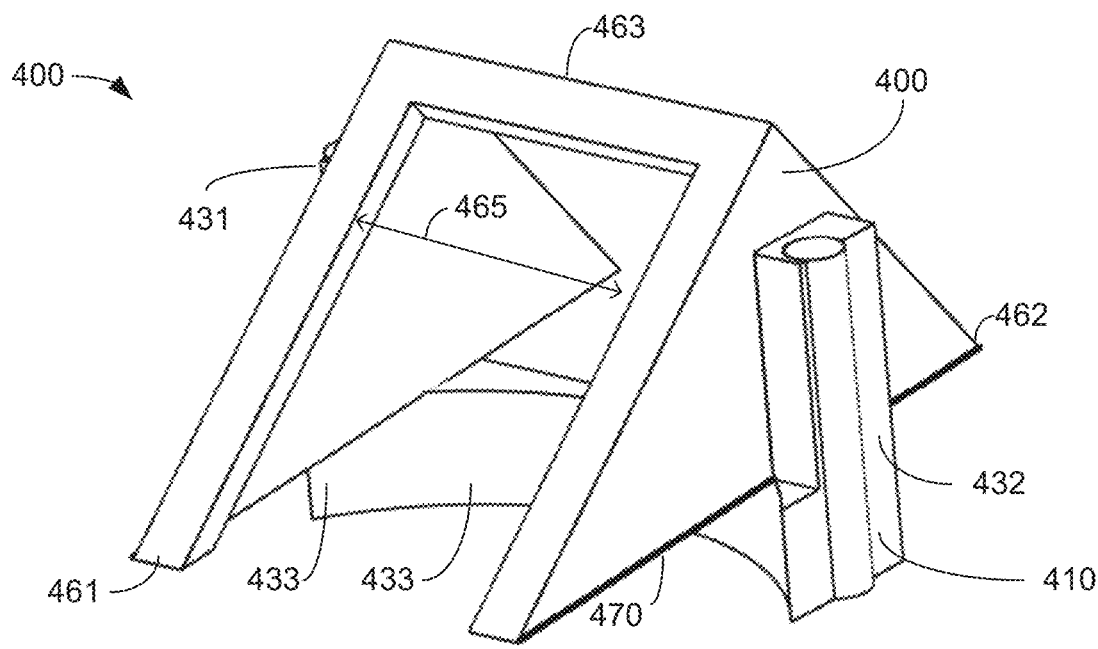
FIG. 15 is a perspective view of a mouthpiece, according to an example embodiment.

Referring now to FIGS. 15, a mouthpiece 400 is shown according to an example embodiment. The mouthpiece 400 may include similar features as the mouthpieces 100, 200 and may provide similar functionality as the mouthpieces 100, 200. For example, the mouthpiece 400 may be used to open a patient's mouth while also protecting the patient's teeth from further damage as a laryngoscope is inserted into the patient's mouth to guide a breathing tube into place in a similar manner as the mouthpieces 100, 200 described above.

As shown, the mouthpiece 400 includes an outer portion 410 and an inner portion 460. As shown, the inner portion 460 is generally wedge shaped. The outer portion 410 includes a first side 431, a second side 432 opposite the first side, and a lower portion 433 that connects the first side 431 to the second side 432. As pictured, the first side 431 is disposed longitudinally opposite from the second side 432. According to various embodiments, the first side 431 is a mirror image of the second side 432, such that the first side 231 and the second side 432 may enable similar functionality. As shown, the lower portion 433 includes a rounded surface 435. The rounded surface 235 is configured to receive a portion of a person's head and neck area (e.g., the chin), as will be discussed further below. Further, the outer portion 410 defines an opening between the first side 431 and the second side 432. This opening is configured to receive the inner portion 460 such that the inner portion 460 may translate within the opening (e.g., as a part of being inserted into a person's mouth).

Figure 16:
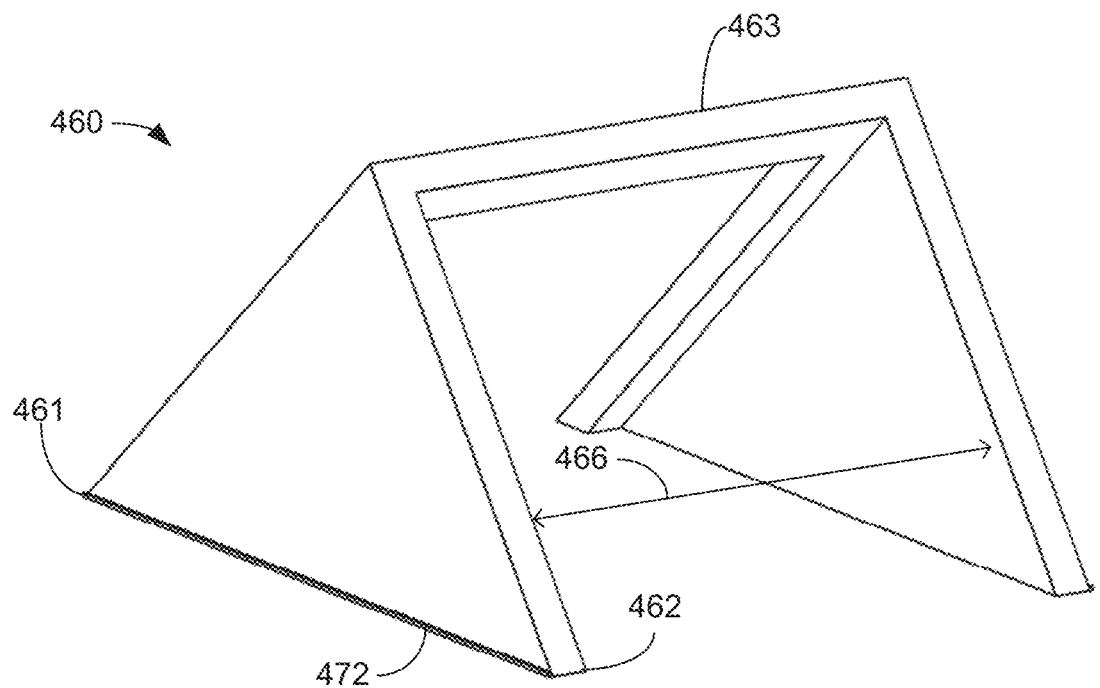
FIG. 16 is a perspective view of the inner portion of the mouthpiece of FIG. 15, according to an example embodiment.
Figure 17:
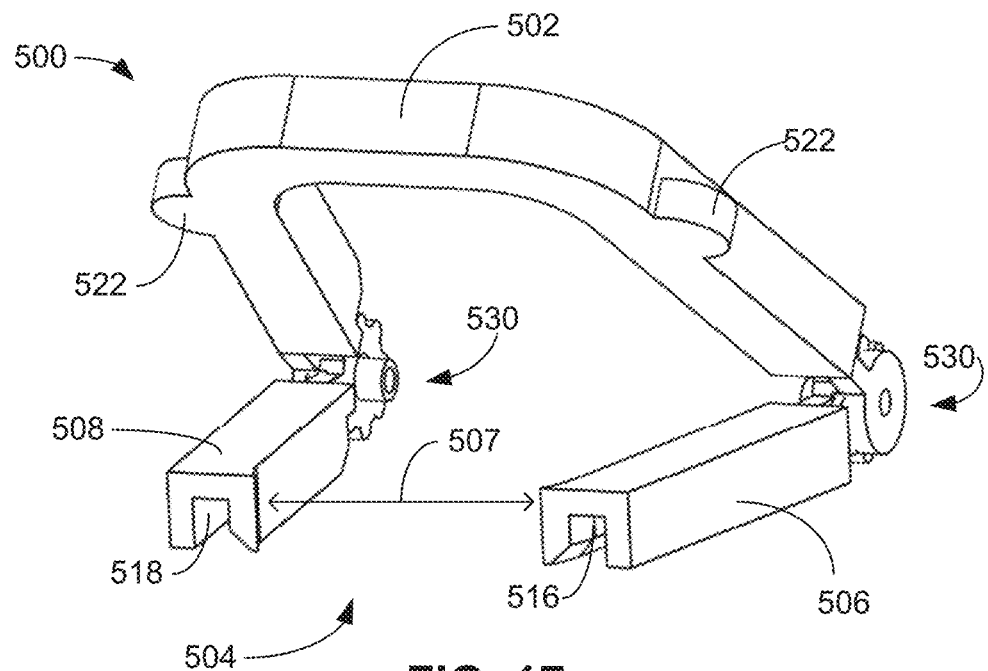
FIG. 17 is a perspective view of a mouthpiece, according to an example embodiment.

Referring now to FIG. 16, the inner portion 460 is shown in greater detail. As shown, the inner portion 460 is generally triangular shaped. In other words, the inner portion 460 generally converges to a point proximate a first end 461 and proximate a second end 462 of the inner portion 460. According to various embodiments, the first end 461 may be inserted into a person's mouth (e.g., as a part of process 308). As a result of the pointed edge at the first end 461, the inner portion 460 may be used to open a person's mouth without having to pry open the mouth using gum supports as described above. Additionally, the inner portion comes to a point at an intermediate position 463 between the first end 461 and the second end 462. Further, the inner portion 460 defines a first opening 465 (see FIG. 15) and a second opening 466 that are large enough to allow a laryngoscope to be inserted into the patient's mouth to guide a breathing tube into place in a similar manner as the mouthpiece while the inner portion 460 is positioned within the person's mouth.

Further, the inner portion 460 includes a first guide rail 470 and a second guide rail 272, respectively. The guide rails 270, 272 are configured to be revived by guide grooves in the outer portions 410, such that a portion of the guide rails 470, 472 translate within the guide grooves while the inner portion 460 translates within the outer portion 410, thereby providing additional stability.

It should be appreciated that some or all of the components of the mouthpiece 400 may be made of any combination of silicone, rubber, and/or any other material approved for use in medical devices, such as ABS, acetal copolymer, delrin, PET-P, flurosint, halar, hydex, kynar, noryl, nylon, PEEK, polycarbonate, polyethlyenes (e.g. LDPE, HDPE, and UHMW), polypropylene homopolymer, PPSU, PSU, radel A, radel R, and Rulon 641.

Referring now to FIGS. 17-20, a mouthpiece 500 is shown according to an example embodiment. The mouthpiece 500 is configured to translate between at least a closed orientation (see e.g., FIG. 24A), and an open orientation (see e.g., FIG. 24C). The mouthpiece 500 is further configured to controllably prevent a person from closing their mouth while the mouthpiece 500 is in the open orientation. For example, during the intubation of a person, it may be desirable to prevent the patient from closing his or her mouth. According to various embodiments, this allows the doctor to have both of his or her hands free to intubate the patient appropriately, as opposed to the doctor using one hand to separate the teeth and keep the mouth open while using the laryngoscope with the other hand trying to insert the breathing tube. Further, the mouthpiece 500 is configured to selectively close in response to a minimum force being applied to at least one tab 522, as is discussed further below.

As shown, the mouthpiece 500 includes an upper portion 502 and a lower portion 504 coupled to the upper portion 502. The lower portion 504 further includes a first leg 506 and a second leg 508 spaced laterally apart from the first leg 506. As shown, the first leg 506 and the second leg 508 define an opening 507 (see FIG. 17). The opening 507 may be large enough to accommodate a medical device (e.g., a breathing tube, a Laryngoscope, etc.) when the mouthpiece 500 is in an open orientation. It should be appreciated that, according to various embodiments, the first leg 506 may be coupled or integrally formed with the second leg 508. In these embodiments, the opening 507 may be smaller than the opening shown in FIGS. 17-20. Additionally, the first leg 506 and the second leg 508 both include a receiving areas 516, 518, respectively. The receiving areas 516, 518 are configured to receive a portion of the person's inner mouth area (e.g., teeth, gums, etc.). For example, when the mouthpiece 500 is inserted into a person's mouth, one or more of the person's lower teeth may be positioned within the receiving areas 516, 518.

As shown, the upper portion 502 includes a receiving area 512 that is are configured to receive a portion of the person's inner mouth area (e.g., teeth, gums, etc.). For example, when the mouthpiece 500 is inserted into a person's mouth, one or more of the person's upper teeth may be positioned within the receiving areas 512. Further, the upper portion 502 includes is shown to include a plurality of tabs 522 positioned on the lateral sides of the upper portion 502. The tabs 522 may be utilized by a person (e.g., medical professional) to transition the mouthpiece 500 from the closed position to the open position and from the open position to the closed position, as is discussed in greater detail below.

Figure 18:
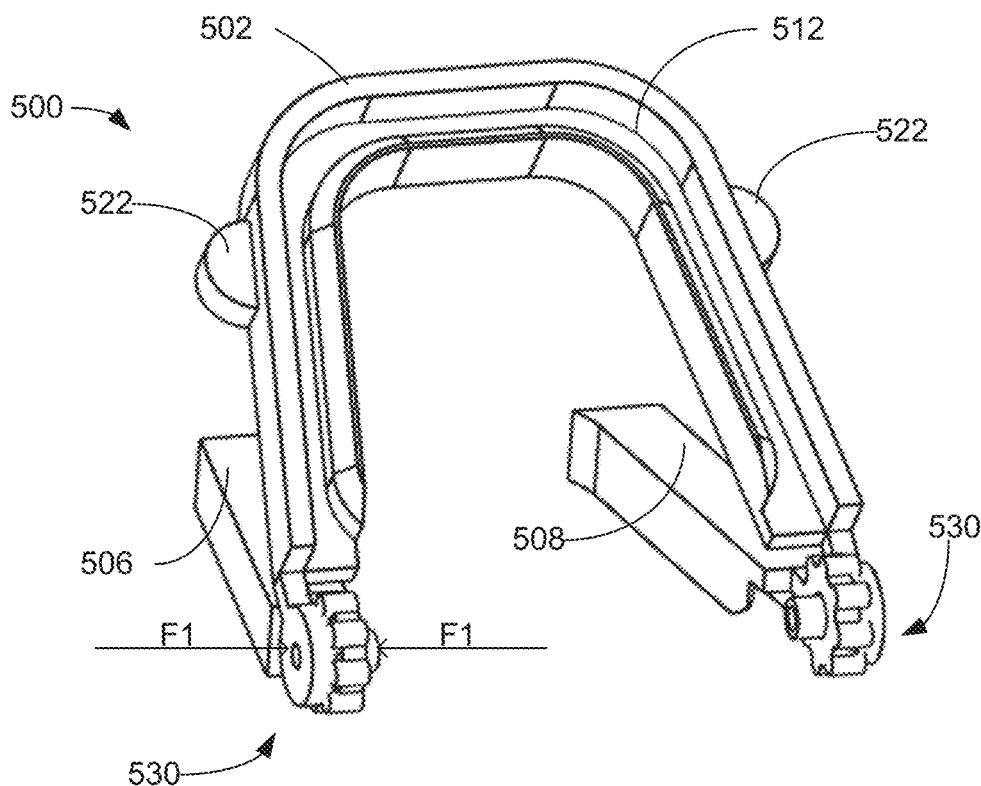
FIG. 18 is another perspective view of the mouthpiece of FIG. 17, according to an example embodiment.
Figure 19:
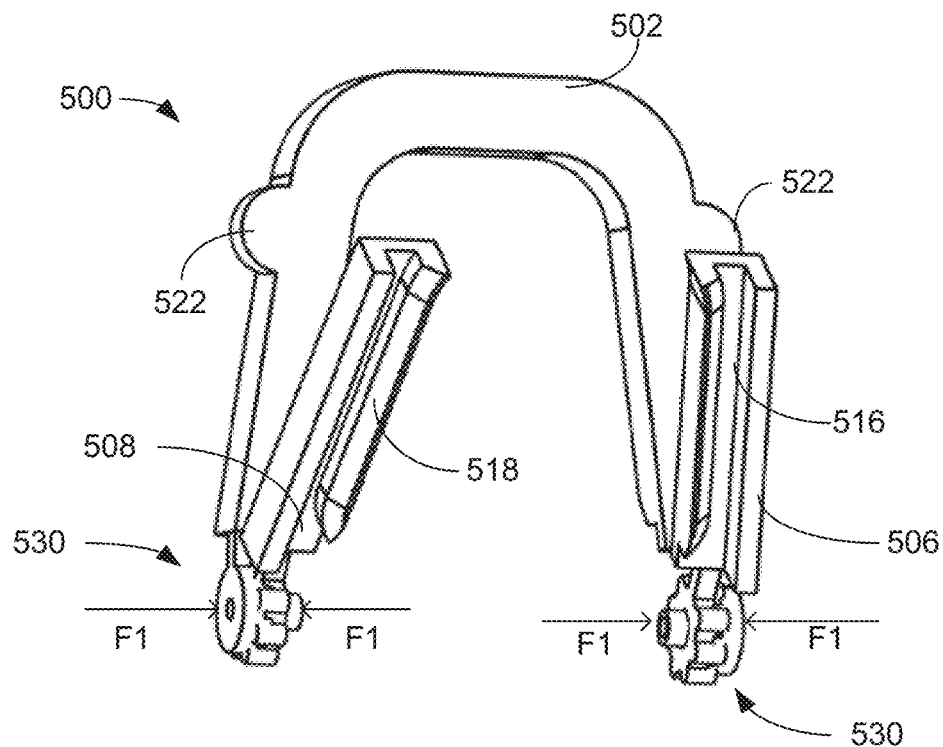
FIG. 19 is another perspective view of the mouthpiece of FIG. 17, according to an example embodiment.
Figure 20:
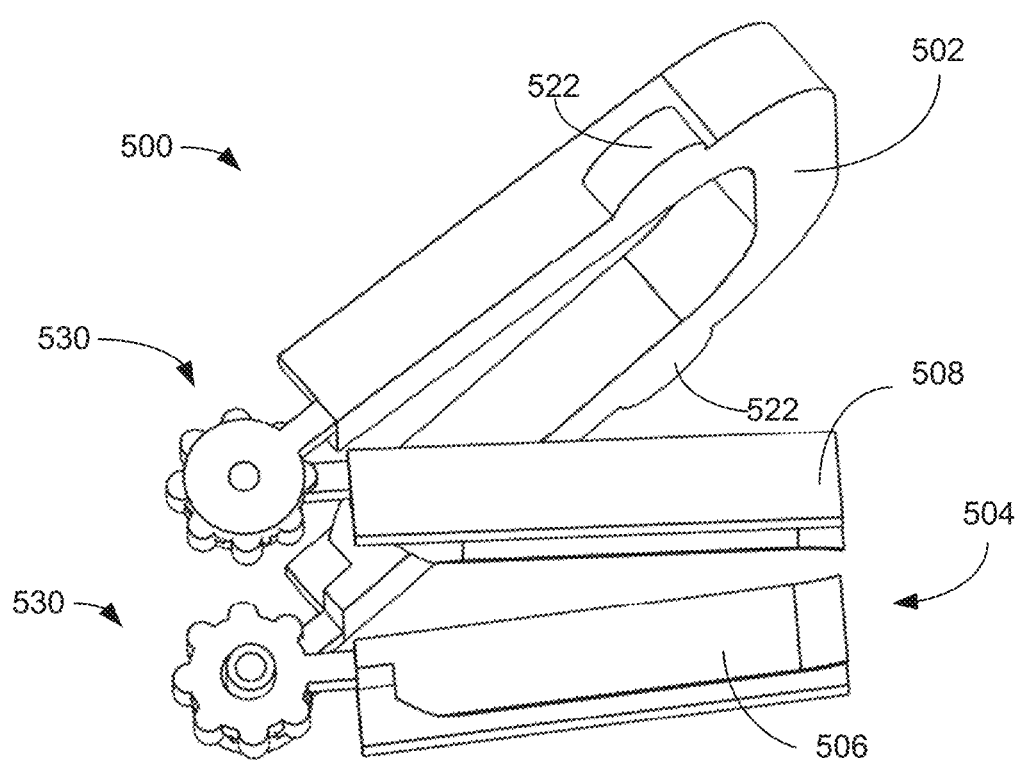
FIG. 20 is another perspective view of the mouthpiece of FIG. 17, according to an example embodiment.

The upper portion 502 is coupled to the first leg 506 and the second leg 508 via a pair of locking mechanisms 530. The locking mechanisms 530 are configured to selectively prevent the mouthpiece 500 from opening and/or closing. For example, the locking mechanisms 530 may allow first leg 506, the second leg 508, and the upper portion 502 to rotate about the locking mechanism 530 when the locking mechanism 530 is in the unlocked position. Once the mouthpiece 500 is in a desired orientation, the locking mechanism 530 may be locked to prevent rotation of the first leg 506, the second leg 508, and the upper portion 502. For example, as shown, the locking mechanisms 530 may be locked by applying a pinching force F1 to the sides of the locking mechanism 530 as shown in FIGS. 18 and 19. As will be discussed further below, applying the force F1 to the locking mechanisms 530 will cause a first locking component 532 to interface with a second locking components 534 to prevent rotation of the first leg 506, the second leg 508, and the upper portion 502.

According to various embodiments, the locking mechanisms 530 are configured to unlock under a predetermined torsional force. For example, if a person were to apply a minimum threshold force on the tabs 522 while the locking mechanisms 530 are locked, the locking mechanisms 530 may unlock, thereby allowing the first leg 506, the second leg 508, and the upper portion 502 to rotate. It should be appreciated that, according to various embodiments, if a similar force is applied to the mouthpiece 500 at a location closer to the locking mechanisms 530, the locking mechanisms 530 may not unlock because the torsional force experienced by the locking mechanism is not sufficient to unlock the locking mechanisms 530. This is because the torsional force experienced by the locking mechanisms 530 is dependent on both the force applied and the perpendicular distance from the applied force to the axis of rotation (e.g., the center of the locking mechanism 530). In general, when a person attempts to close his or her mouth while the mouthpiece 500 is located within their mouth, the person's rear teeth will apply a higher force to the mouthpiece 500 than the person's front teeth. Thus, if a person attempts to close his or her mouth while the mouthpiece 500 is in the open position and the locking mechanisms 530 are locked, the mouthpiece 500 may not close. This is because a majority of the force applied by the person's mouth to the mouthpiece 500 is closer to the axis of rotation than the tabs 522. Thus, the locking mechanisms 530 may prevent a person from unlocking the locking mechanisms 530 by bighting down on the mouthpiece 500, while also allowing a person to press on the tabs 522 to generate a sufficient torsional force to unlock the locking mechanisms 530 and close the mouthpiece 500.

Figure 21:
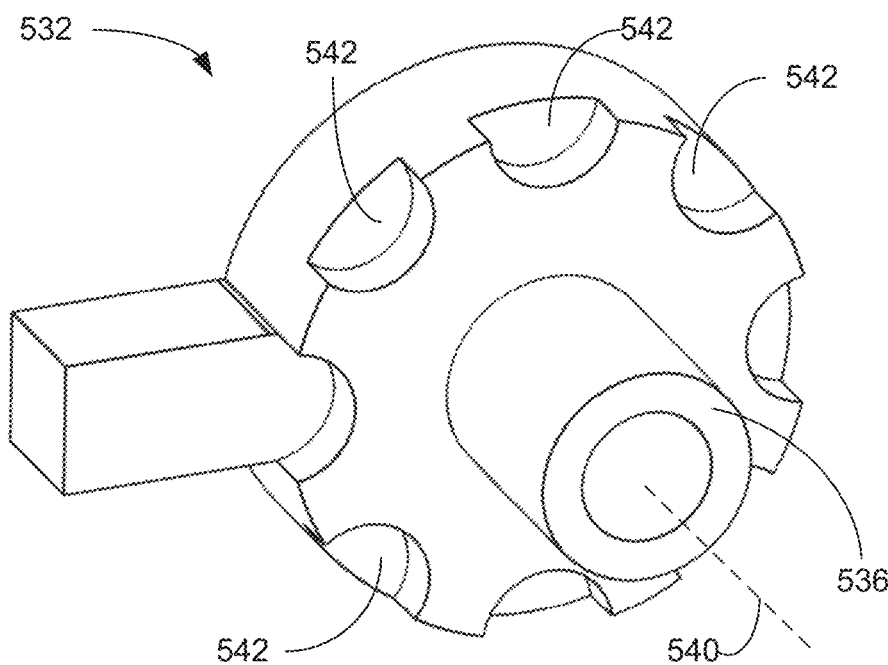
FIG. 21 is a perspective view of a locking component of FIG. 17, according to an example embodiment.
Figure 22:
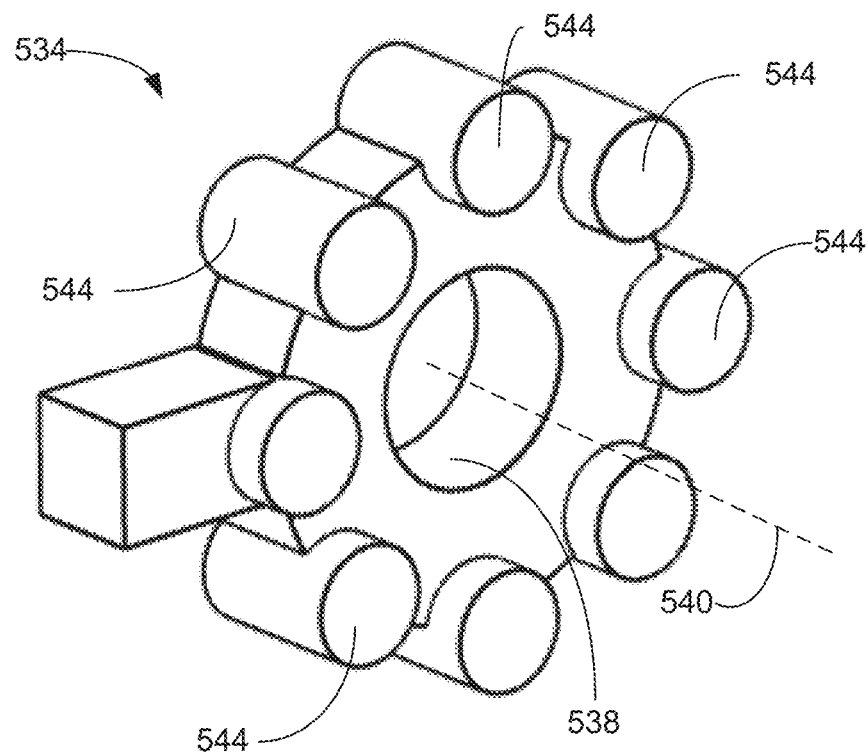
FIG. 22 is a perspective view of another locking component of FIG. 17, according to an example embodiment.

Referring now to FIGS. 21 and 22, the first locking component 532 and the second locking component 534 are shown in greater detail. According to various embodiments, the first locking component 532 and the second locking component 534 are included in the locking mechanisms 530 discussed above. As shown, the first locking component 532 includes a protrusion 536 that is configured to be received by an aperture 538 in the second locking component 534 such that the first locking component 532 and the second locking component 534 can rotate about a central axis 540. Further, the first locking component 532 includes a plurality of indentations 542 that are configured to receive a plurality of projections 544 of the second locking component 534. For example, as discussed above, if a person were to apply a pinching force (e.g., F1 shown in FIG. 19), the projections 544 may be positioned within the indentations 542, thereby preventing the first locking component 532 from rotating relative to the second locking component 534. However, as discussed above, if the locking mechanism 530 experiences a sufficient torsional force, the locking mechanism 530 may unlock, thereby allowing the first locking component 532 and the second locking component 534 to rotate about the central axis 540. According to various embodiments, when the locking mechanism 530 experiences sufficient torsional force, the projections 544 may slip, bend, or deform, thereby separating the first locking component 532 from the second locking component 534, which causes the locking mechanism 530 to unlock. According to various embodiments, the first locking component 532 and the second locking mechanism are manufactured from a plastic material.

While FIGS. 21 and 22 show components of an example locking mechanism 530, it should be appreciated that other types of locking mechanisms 530 may be included. For example, the locking mechanism 530 may include a ratcheting mechanism, a spring mechanism (e.g., a torsional spring), a solid piece of material configured to fracture and/or fail under a certain torsional load, or any combination thereof. Thus, the locking mechanism 530 shown is meant to be exemplary in nature and should not be construed as limiting.

Figure 23:
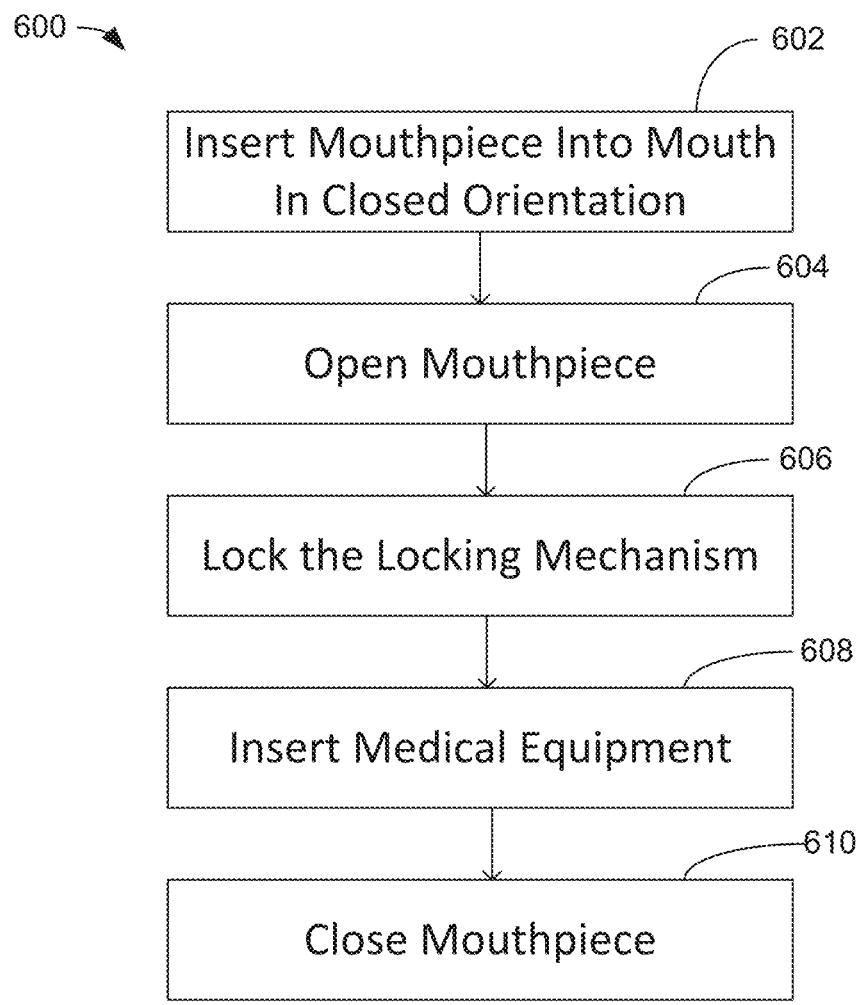
FIG. 23 is a block diagram of a mouth opening process, according to an example embodiment.

Referring now to FIG. 23, a block diagram of mouth opening process 600 is shown, according to an example embodiment. The process 600 contemplates using some or all of the mouthpieces (e.g., the mouthpiece 500) described herein. The process 600 may be used, for example, to insert a breathing tube. It should be appreciated that the process 600 need not be performed in the order shown, certain process may be omitted, and additional processes may be included.

As shown, process 600 includes process 602, which involves inserting the mouthpiece into a person's mouth in the closed position. Once the mouthpiece is inserted into the mouth, the mouthpiece can be opened as a part of process 604. For example, a person may apply an upwards force on the tabs 522 and a downward force on the lower portion 504 to open the mouthpiece 500. Once the mouthpiece is open, the mouthpiece is then locked in the open position within the person's mouth as a part of process 606. For example, a person may apply a force F1 to the locking mechanism 530 to lock the mouthpiece 500 in the open position. Once locked in the open position, medical equipment (e.g., a breathing tube) may be inserted into the person's mouth while the mouthpiece holds the person's mouth open, as a part of process 608. Once the mouth is open, the jaw will be locked open (e.g., to insert the breathing tube) until the locking mechanism 530 experiences sufficient torsional force to collapse the mouthpiece 500 (e.g., as a result of a doctor applying a downward force on the tabs 522).

Finally, once the person's mouth no longer needs to be help open, the mouthpiece is closed as a part of process 610. For example, as discussed above, a person may apply sufficient force to the tabs 522 to cause a sufficient torsional force in the locking mechanism 530 to unlock the locking mechanism 530, thereby allowing the mouthpiece 500 to close, such that mouthpiece may then be removed from the person's mouth.

Figure 24A:
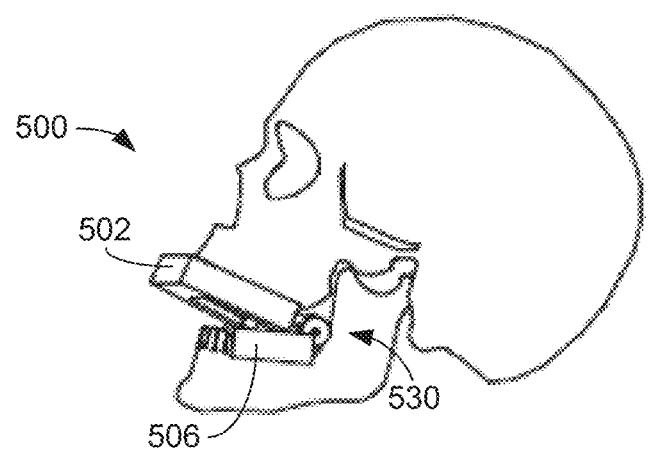
FIGS. 24A-C are visual representations of the mouthpiece of FIG. 17 being used to open a person's mouth, according to an example embodiment.
Figure 24B:
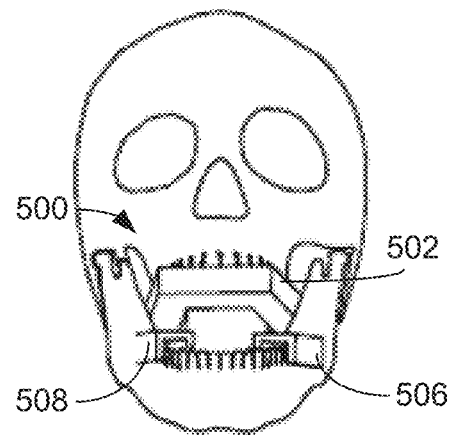
Figure 24C:
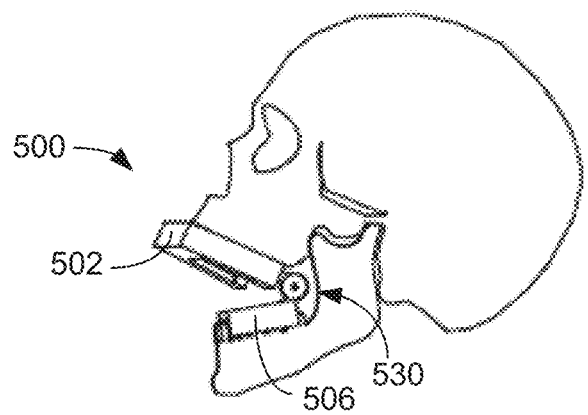
Figure 25:
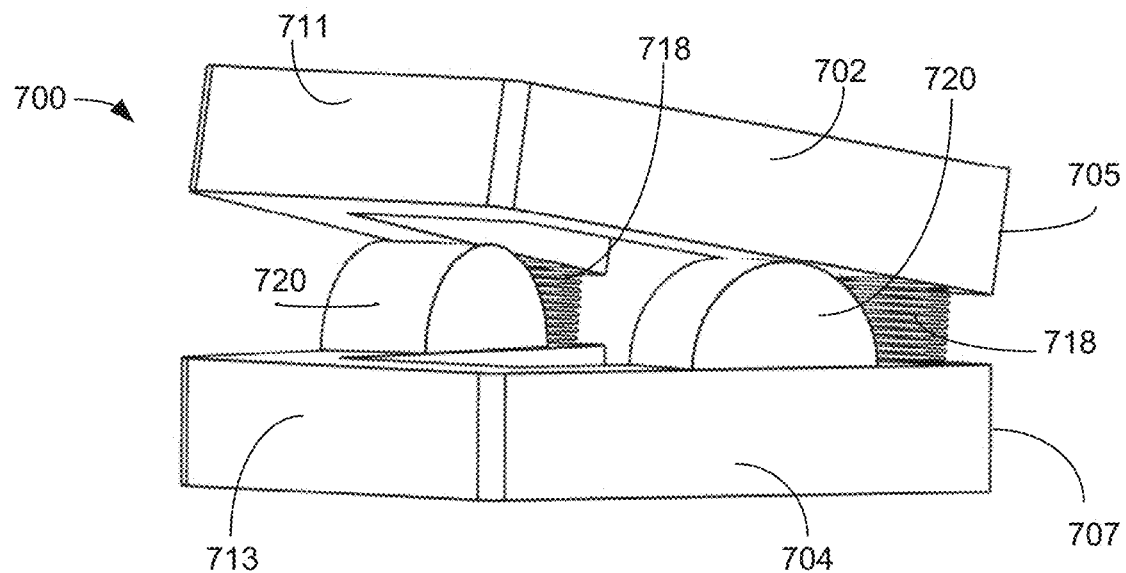
FIG. 25 is a perspective view of a mouthpiece, according to an example embodiment.

Referring now to FIGS. 24A-24C, a visual representation of the mouthpiece 500 being used to open a person's mouth is shown, according to an example embodiment. For example, FIGS. 24A and 24B may correspond with process 602 and FIG. 24C may correspond with process 604 and 606. As shown in FIGS. 24A and 24B, the mouthpiece 500 is inserted into a person's mouth in the closed orientation. The mouthpiece 500 may then be opened and locked in the open position, as shown in FIG. 24C, thereby further keeping the persons mouth open and keeping the mouth open.

It should be appreciated that some or all of the components of the mouthpiece 500 may be made of any combination of silicone, rubber, and/or any other material approved for use in medical devices, such as ABS, acetal copolymer, delrin, PET-P, flurosint, halar, hydex, kynar, noryl, nylon, PEEK, polycarbonate, polyethlyenes (e.g. LDPE, HDPE, and UHMW), polypropylene homopolymer, PPSU, PSU, radel A, radel R, and Rulon 641.

Referring now to FIGS. 25-32, a mouthpiece 700 is shown, according to an example embodiment. The mouthpiece 700 is configured to be cause separation between the rear portion of the upper and lower jaw such that the mouthpiece 700 can be used to facilitate a manual reduction of a person's jaw (e.g., as a part of treating a dislocated jaw), as is discussed in further detail below.

As shown, the mouthpiece 700 includes an upper portion 702 and a lower portion 704 coupled to the upper portion 702. As shown, the upper portion 702 includes a receiving area 712 that is are configured to receive a portion of the person's inner mouth area (e.g., teeth, gums, etc.). For example, when the mouthpiece 500 is inserted into a person's mouth, one or more of the person's upper teeth may be positioned within the receiving areas 512. The lower portion 704 includes a receiving area 716 that is configured to receive a portion of the person's inner mouth area (e.g., teeth, gums, etc.). For example, when the mouthpiece 700 is inserted into a person's mouth, one or more of the person's lower teeth may be positioned within the receiving area 716.

Figure 26:
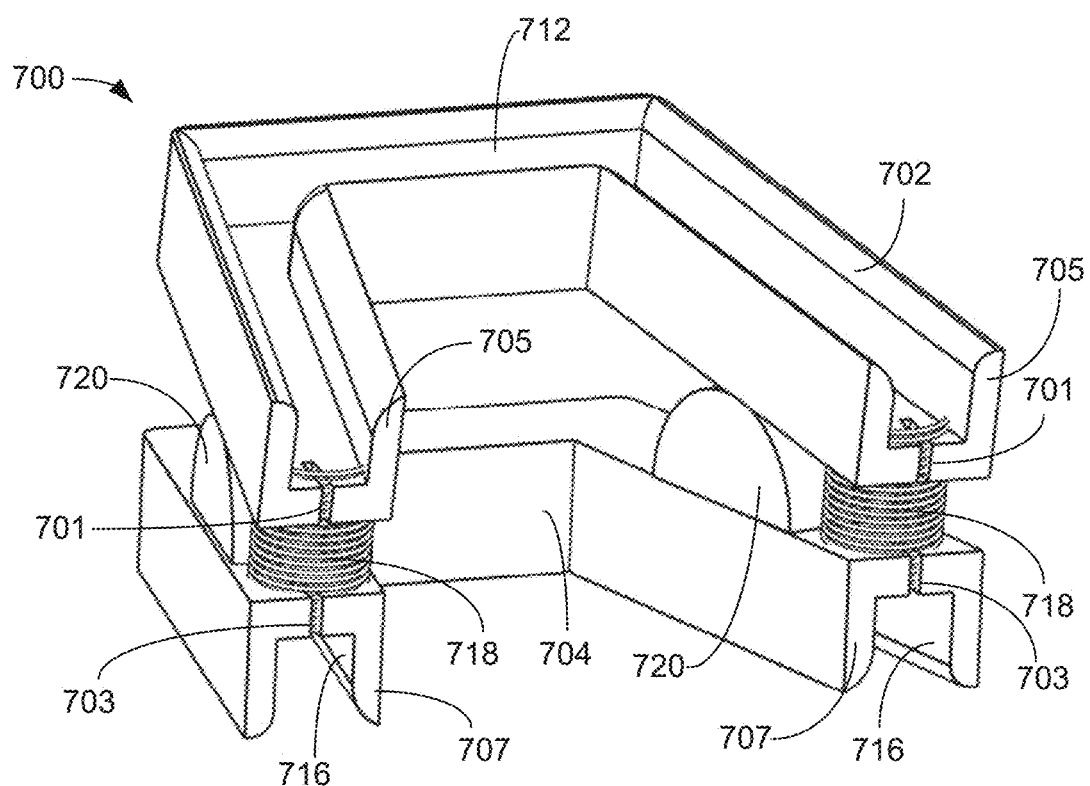
FIG. 26 is another perspective view of the mouthpiece of FIG. 25, according to an example embodiment.
Figure 27:
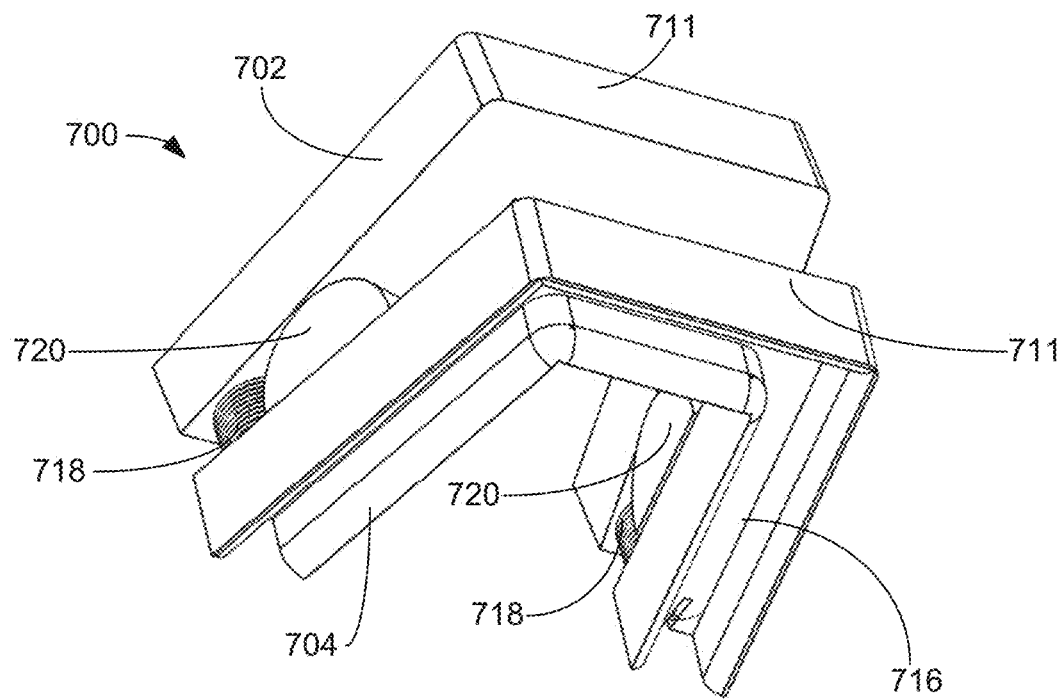
FIG. 27 is another perspective view of the mouthpiece of FIG. 25, according to an example embodiment.
Figure 28:
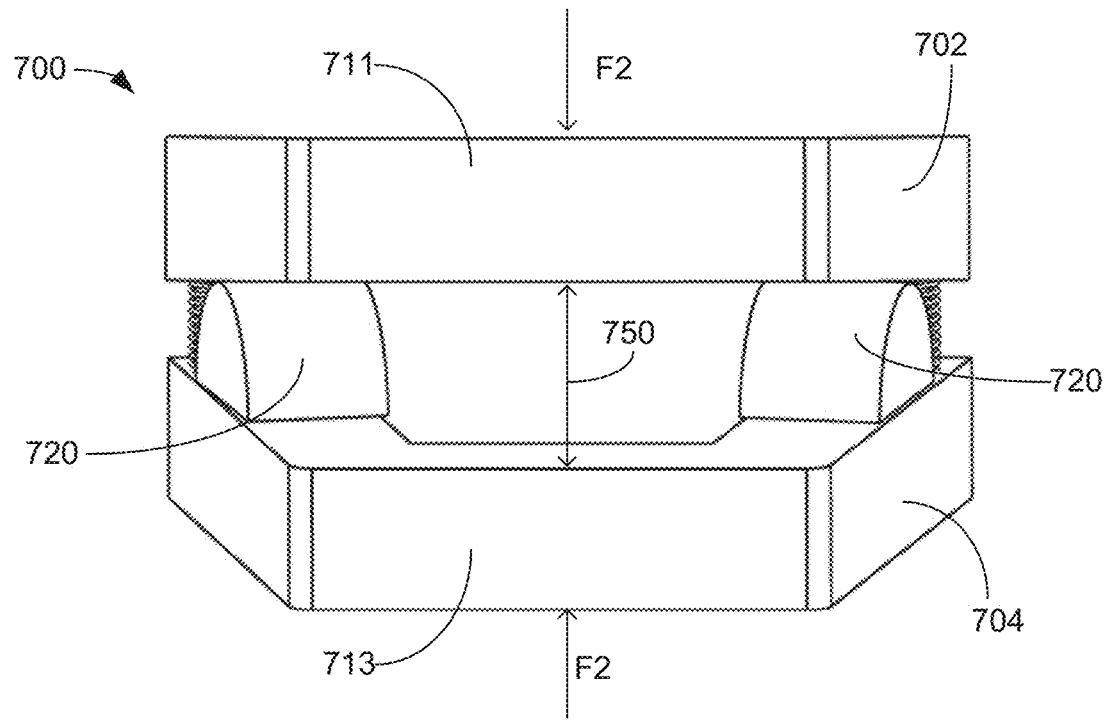
FIG. 28 is another perspective view of the mouthpiece of FIG. 25, according to an example embodiment.
Figure 29:
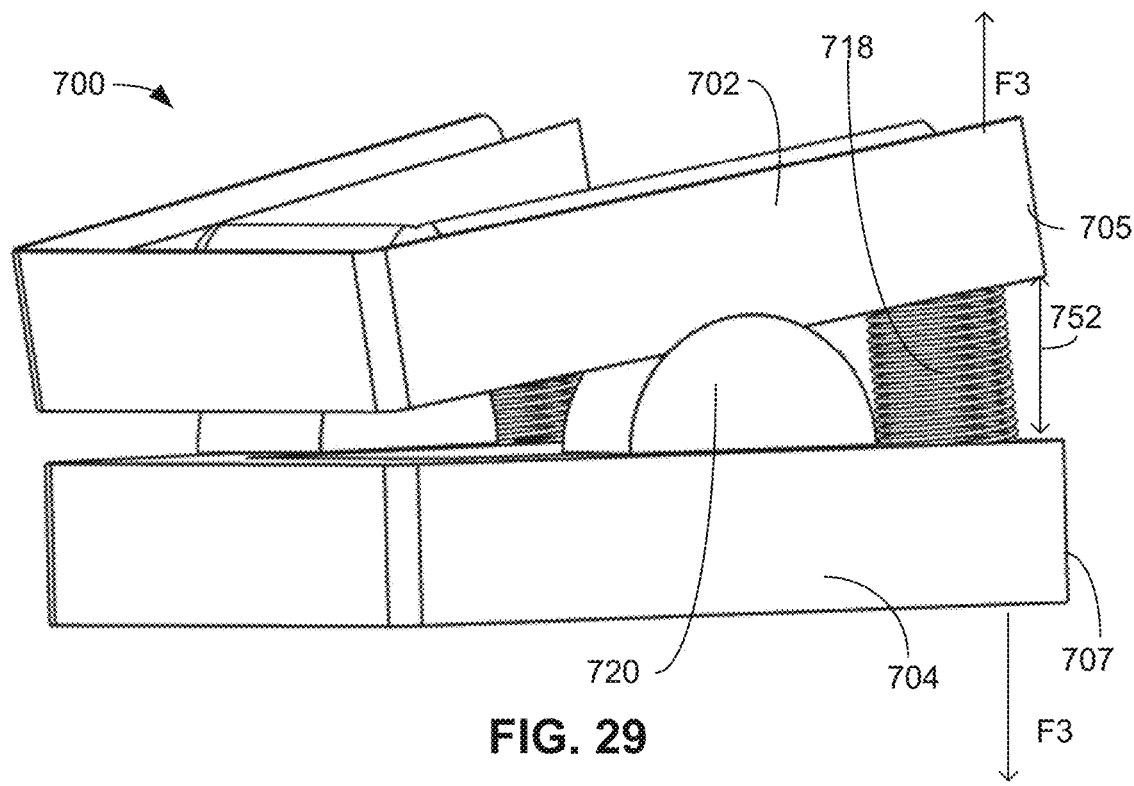
FIG. 29 is another perspective view of the mouthpiece of FIG. 25, according to an example embodiment.
Figure 30:
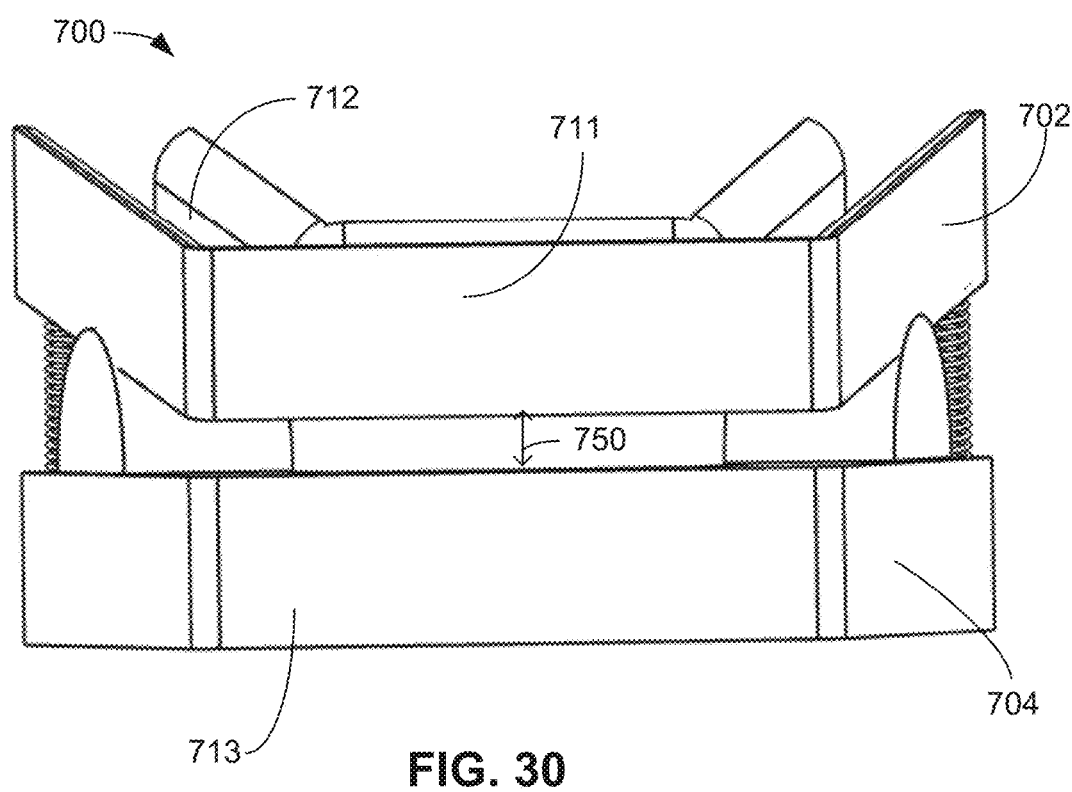
FIG. 30 is another perspective view of the mouthpiece of FIG. 25, according to an example embodiment.
Figure 31:
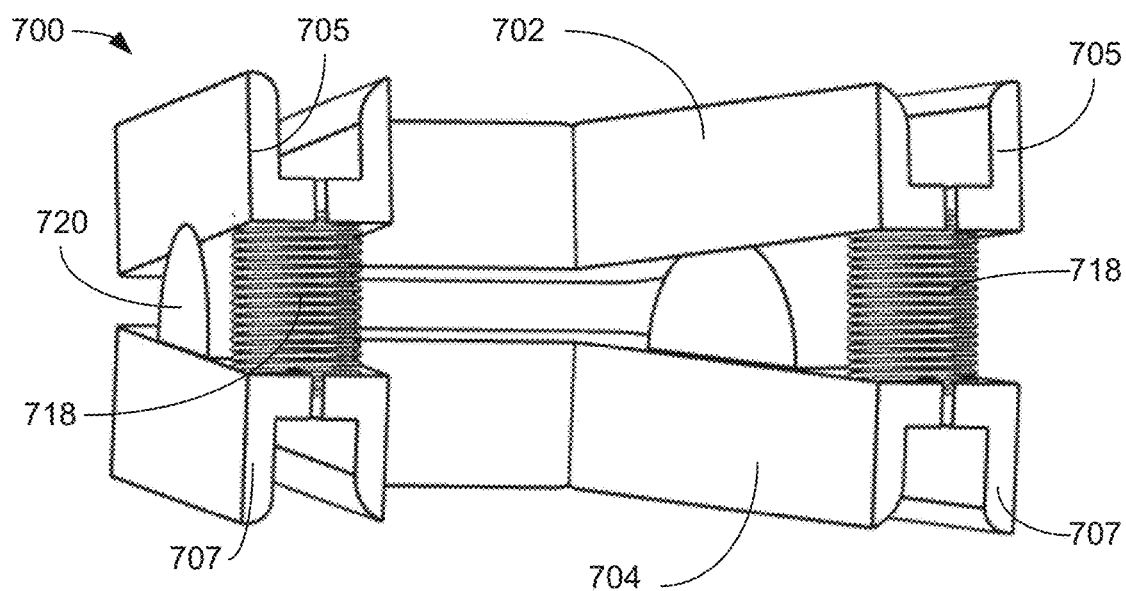
FIG. 31 is another perspective view of the mouthpiece of FIG. 25, according to an example embodiment.
Figure 32:
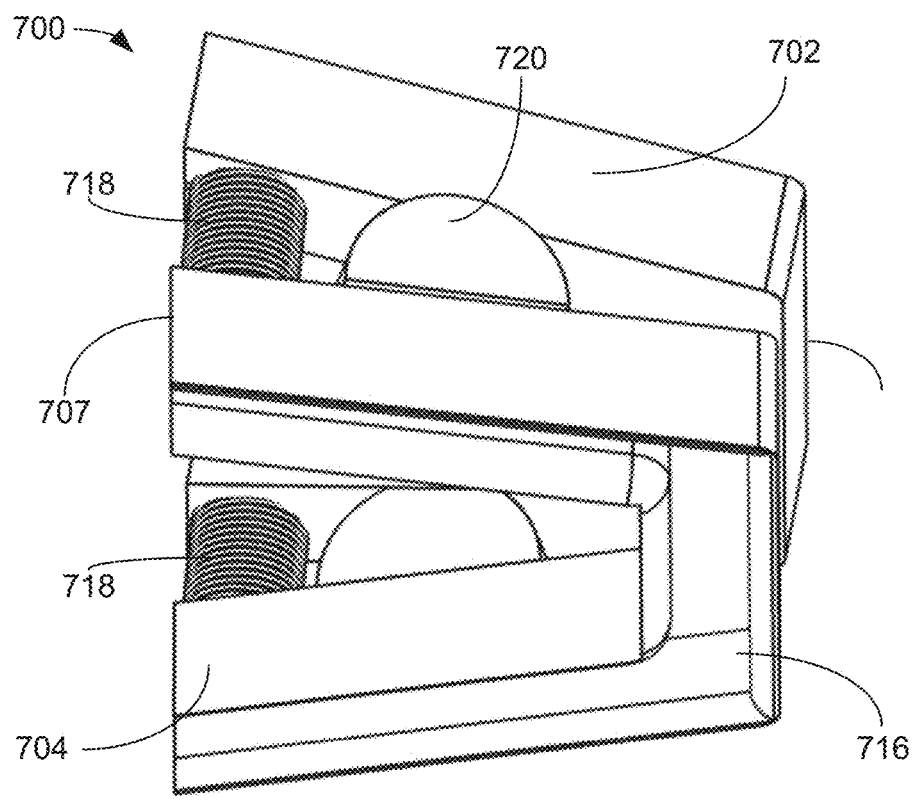
FIG. 32 is another perspective view of the mouthpiece of FIG. 25, according to an example embodiment.

The mouthpiece 700 further includes a plurality of connecting members 718 that couple the upper portion 702 to the lower portion 704 proximate a rear end 705 of the upper portion 702 and a rear end 707 of the lower portion. The connecting members 718 are shown as springs in this example embodiment, however, it should be appreciated that the connecting members 718 may be other types of flexible material, such as thread, string, nylon, elastic material, rubber material, flexible plastic material, etc. The connecting members 718 are configured to allow traverse movement of the lower portion 704 relative to the upper portion 702, as is discussed further below. As shown in FIG. 26, the connecting members 718 are retained within slits 701 in the upper portion 702 and slits 703 in the lower portion 704. However, in other embodiments, the connecting members 718 may be coupled to the upper portion 702 and the lower portion 704 in a different manner (e.g., integrally formed, adhesive, fasteners, etc.).

The mouthpiece 700 further includes a plurality of support members 720 coupled to the lower portion 704. The support members 720 are configured to maintain space between the upper portion 702 and the lower portion 704 such that the support member acts as a fulcrum. For example, when the mouthpiece 700 is in a first orientation (e.g., the orientation shown in FIGS. 25-28), and a pinching force (e.g., pinching force F2 shown in FIG. 28) is applied to a front end 711 of the upper portion 702 and a front end 713 of the lower portion 704, the distance 750 between the front ends 711, 713 will decrease (see e.g., FIG. 30), while the distance 752 between the rear ends 705, 707 increases (see FIG. 29), thereby repositioning the mouthpiece 700 in a second orientation (e.g., the orientation shown in FIGS. 29-32). Therefore, when the mouthpiece 700 is positioned in a desired location in a person's mouth, when the pinching force F2 is applied, the mouthpiece 700 will exert an expanding force F3 (see FIG. 29) near the back of a person's mouth, as is discussed further below. It should be appreciated that, while the support member 720 shown is a semi-circular support member with a rounded surface that interfaces with the upper portion 702, according to various embodiments, the support members 720 may be a different shape (e.g., triangular, rectangular, hexagonal, etc.) and may be coupled to the upper portion 702 instead of the lower portion 704.

Figure 33:
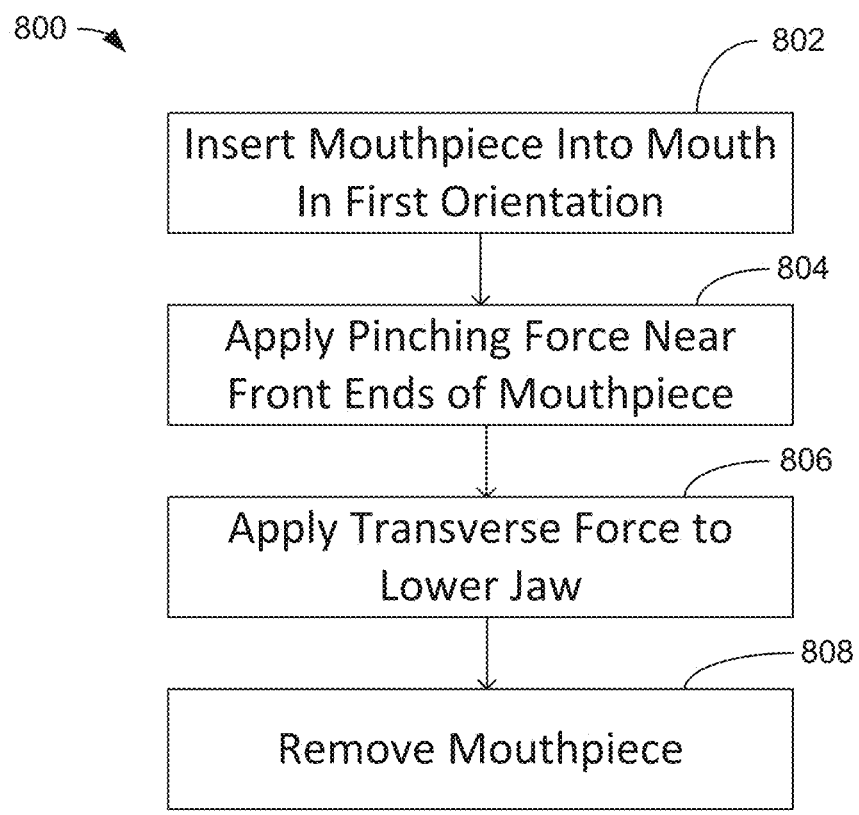
FIG. 33 is a block diagram of a jaw relocating process, according to an example embodiment.

Referring now to FIG. 33, a block diagram of a jaw relocating process 800 is shown, according to an example embodiment. The process 800 contemplates using some or all of the mouthpieces (e.g., the mouthpiece 700) described herein. It should be appreciated that the process 800 need not be performed in the order shown, certain process may be omitted, and additional processes may be included.

In generally, treating a dislocated jaw may present a number of difficulties. For example, a dislocated jaw may occurs when the mandible bone becomes detached from one or both of the temporomandibular joints (TMJs), which allow the jaw to open and close. A medical professional may treat a dislocated jaw by manually repositioning the mandible bone back within the TMJs. This process may be referred to as a manual reduction. As a part of a manual reduction, the medical professional may place their thumbs against the lower back teeth inside the mouth and their remaining fingers under the jaw. The medical professional may then apply a downward force in the coronal plane to the jaw and proceed to put the mandible bone back within the TMJs by applying a forward and/or backwards force in the transverse plane. However, it may be difficult for a medical professional to position his or her hands within the inside of the person's mouth to apply the downward force in the coronal plane. Additionally, placing the hands within the patient's mouth puts the medical professional at risk of injury (e.g., as a result of being bitten). However, the process 800 may be used to apply the downward force to the mandible bone in the coronal plane without requiring the medical professional to place his or her hands in the person's mouth.

As shown, process 800 includes process 802, which involves inserting the mouthpiece into a person's mouth. For example, the mouthpiece 700 may be inserted into the person's mouth in a first orientation (e.g., the orientation shown in FIGS. 25-28). Once the mouthpiece is inserted into the mouth, a pinching force may be applied to the front ends of the mouthpiece as a part of process 804. For example, a medical professional may apply a pinching force F2 to the front ends 711, 713 of the mouthpiece 700 (see FIG. 28). According to various embodiments, the pinching force F2 may cause the mouthpiece 700 to transform to the second orientation (e.g., the orientation shown in FIGS. 29-32). Further, as is discussed above, applying the pinching force F2 may cause a separating force F3 (see FIG. 29) at the rear ends 705, 707, thereby generating a downward force in the coronal plane to the mandible bone. After applying the pinching force near the front ends of the mouthpiece, a transverse force may be applied to the lower jaw (e.g., the mandible bone) as a part of process 806. For example, a medical professional may apply a forward and/or backwards force to the jaw (e.g., the chin, sides of the mandible, etc.) of the person to relocate the mandible bone back within the TMJs. Alternatively or additionally, the medical professional may apply a transverse force to the lower portion 704 of the mouthpiece 700, which will in turn apply a transverse force to the mandible bone. Once the jaw is relocated, the mouthpiece may be removed as a part of process 808.

Figure 34A:
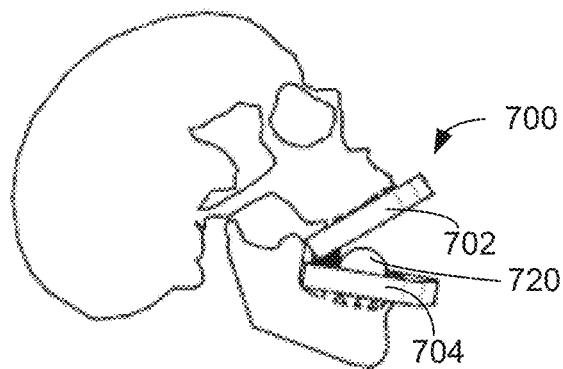
FIGS. 34A-C are visual representations of the mouthpiece of FIG. 25 being used to relocate a person's jaw, according to an example embodiment.
Figure 34B:
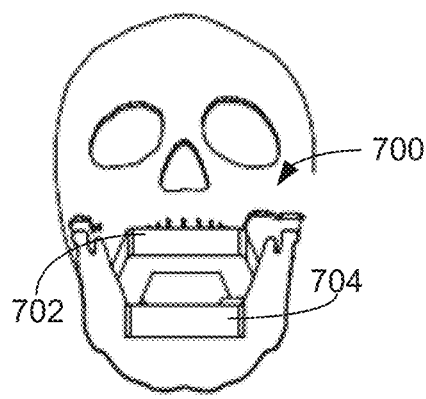
Figure 34C:
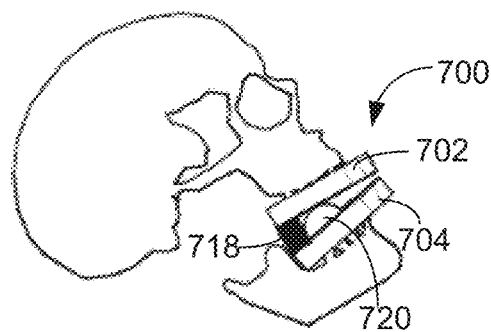

Referring now to FIGS. 34A-34C, a visual representation of the mouthpiece 700 being used to relocate a jaw is shown, according to an example embodiment. For example, FIGS. 34A and 34B may correspond with process 802 and FIG. 34C may correspond with process 804. As shown in FIGS. 34A and 34B, the mouthpiece 700 is inserted into a person's mouth in the first orientation. As shown in FIG. 34C, a pinching force is applied to the front ends of the mouthpiece 700, which causes the mouthpiece 700 to transform into the second orientation. Once in the second orientation, a transverse force may be applied to the person's mandible to relocate his or her jaw.

It should be appreciated that some or all of the components of the mouthpiece 200 may be made of any combination of silicone, rubber, and/or any other material approved for use in medical devices, such as ABS, acetal copolymer, delrin, PET-P, flurosint, halar, hydex, kynar, noryl, nylon, PEEK, polycarbonate, polyethlyenes (e.g. LDPE, HDPE, and UHMW), polypropylene homopolymer, PPSU, PSU, radel A, radel R, and Rulon 641.

As utilized herein with respect to numerical ranges, the terms "approximately," "about," "substantially," and similar terms generally mean+/−10% of the disclosed values unless otherwise specified. When the terms "approximately," "about," "substantially," and similar terms are applied to a structural feature (e.g., to describe its shape, size, orientation, direction, etc.), these terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the mouthpiece as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed:

1. A mouthpiece comprising:
   an outer portion comprising a first side, a second side, and a lower portion, wherein the lower portion spans between the first side and the second side;
   a first pillar coupled to the first side and configured to rotate about a first axis;
   a second pillar coupled to the second side and configured to rotate about a second axis;
   a first upper gum support coupled to the first pillar and configured to rotate about a third axis that is perpendicular to the first axis;
   a first lower gum support coupled to the first pillar and configured to rotate about a fourth axis that is perpendicular to the first axis;
   a second upper gum support coupled to the second pillar and configured to rotate about a fifth axis that is perpendicular to the second axis; and
   a second lower gum support coupled to the second pillar and configured to rotate about a sixth axis that is perpendicular to the second axis.

2. The mouthpiece of claim 1 further comprising an inner wedge configured to be received within the first side and the second side of the outer portion, wherein a lower surface of the inner wedge in configured to be received by the lower portion of a mouth.

3. The mouthpiece of claim 2, wherein the inner wedge comprises an inner primary opening configured to receive a laryngoscope.

4. The mouthpiece of claim 2, wherein the lower portion includes a curved surface configured to receive a lower portion of a person's face.

5. The mouthpiece of claim 2, wherein the inner wedge includes a plurality of guide rails configured to be received within a plurality of guide grooves in the outer portion.

6. The mouthpiece of claim 2, wherein the inner wedge further includes a protrusion extending from an upper surface of the inner wedge, wherein the inner wedge is configured to engage a front portion of a person's mouth.

7. The mouthpiece of claim 1, further comprising:
a first sanitary cap coupled to an end of the first upper gum support;
a second sanitary cap coupled to an end of the second upper gum support;
a third sanitary cap coupled to an end of the first lower gum support; and
a fourth sanitary cap coupled to an end of the second lower gum support.

8. A mouthpiece comprising:
an upper portion configured to receive an upper portion of a person's mouth;
a lower portion configured to receive a lower portion of the person's mouth and rotatably coupled to the upper portion via a hinge such that the mouthpiece is configured to transform between at least an open orientation and a closed orientation; and
a locking mechanism coupled to the upper portion and the lower portion, wherein the locking mechanism is configured to:
prevent the upper portion from rotating relative to the lower portion when the locking mechanism is in a locked orientation, and
allow the upper portion to rotate relative to the lower portion when the locking mechanism is in an unlocked orientation,
wherein the locking mechanism is configured to transform from the locked orientation to the unlocked orientation in response to experiencing a threshold torsional force.

9. The mouthpiece of claim 8, wherein the locking mechanism is configured to transform from the unlocked to the locked orientation in response to a pinching force being applied to the locking mechanism.

10. The mouthpiece of claim 8, wherein the locking mechanism is positioned proximate a rear portion of the mouthpiece; and
wherein the upper portion includes a first tab proximate the front end of the mouthpiece.

11. The mouthpiece of claim 10, wherein the upper portion includes a second tab proximate the front end of the mouthpiece.

12. The mouthpiece of claim 10, wherein the locking mechanism is configured to transform from the locked to unlocked position in response to a minimum threshold force being applied to the first tab.

13. The mouthpiece of claim 8, wherein the locking mechanism comprises:
a first locking components including a plurality of indentations; and
a second locking component including a plurality of projections configured to be received by the plurality of indentations when the locking mechanism is in the locked orientation.

14. The mouthpiece of claim 13, wherein the plurality of projections are positioned outside the plurality of indentations when the locking mechanism is in the unlocked orientation.

15. A mouthpiece comprising:
an upper portion including a front end configured to receive a front portion of a human mouth and a rear end configured to extend into the human mouth;
a lower portion including a front end configured to receive the front portion of the human mouth and a rear end configured to extend into the human mouth and coupled to the upper portion by a connecting member; and
a support member coupled to the lower portion between the front end and the connecting member, such that applying a pinching force to the front end of the upper portion and the front end of the lower portion causes the rear end of the upper portion to move away from the rear end of the lower portion, wherein the support member comprises a semi-circular support member with a rounded surface that interfaces with the upper portion.

16. The mouthpiece of claim 15, further comprising a first connecting member that couples the rear end of the upper portion to the rear end of the lower portion.

17. The mouthpiece of claim 16, wherein the first connecting member includes a spring.

18. The mouthpiece of claim 17, further including a second connecting member that couples the rear end of the upper portion to the rear end of the lower portion.

* * * * *